US012606858B2

(12) United States Patent
Leder et al.

(10) Patent No.: US 12,606,858 B2
(45) Date of Patent: Apr. 21, 2026

(54) METHODS, KITS AND DEVICES FOR MEASURING EXTRACELLULAR PYRIDINE NUCLEOTIDE

(71) Applicant: Charite—Universitaetsmedizin Berlin, Berlin (DE)

(72) Inventors: Annekatrin Leder, Berlin (DE); Philipp Brunnbauer, Berlin (DE); Felix Krenzien, Berlin (DE)

(73) Assignee: Charité—Universitäetsmedizin Berlin, Berlin (DE)

( * ) Notice: Subject to any disclaimer, the term of this patent is extended or adjusted under 35 U.S.C. 154(b) by 912 days.

(21) Appl. No.: 17/017,733

(22) Filed: Sep. 11, 2020

(65) Prior Publication Data

US 2021/0087603 A1     Mar. 25, 2021

Related U.S. Application Data

(60) Provisional application No. 62/903,111, filed on Sep. 20, 2019.

(51) Int. Cl.
*C12Q 1/32*      (2006.01)
*C12Q 1/26*      (2006.01)

(52) U.S. Cl.
CPC ................. *C12Q 1/32* (2013.01); *C12Q 1/26* (2013.01); *G01N 2333/395* (2013.01); *G01N 2333/902* (2013.01); *G01N 2333/904* (2013.01); *G01N 2400/00* (2013.01); *G01N 2496/00* (2013.01)

(58) Field of Classification Search
CPC ...... C12Q 1/32; C12Q 1/26; G01N 2333/904; G01N 2400/00; G01N 2496/00; G01N 2333/902; G01N 2333/395
See application file for complete search history.

(56) References Cited

U.S. PATENT DOCUMENTS

| | | | | |
|---|---|---|---|---|
| 5,141,854 A | * | 8/1992 | Kaufman ................. | C12Q 1/32 435/26 |
| 5,723,496 A | * | 3/1998 | Nakada .............. | A61K 31/5375 514/634 |
| 6,287,796 B1 | | 9/2001 | Jacobson et al. | |
| 2002/0066699 A1 | * | 6/2002 | Boggs ................ | B01D 69/1411 210/488 |
| 2004/0019431 A1 | * | 1/2004 | Sterling ............... | A61B 5/1455 702/19 |
| 2004/0029171 A1 | * | 2/2004 | Wagner .................. | A61B 5/145 435/7.1 |
| 2007/0196520 A1 | * | 8/2007 | Lin ........................ | A61K 36/54 424/739 |
| 2010/0159495 A1 | * | 6/2010 | Vormbrock .............. | C12Q 1/48 435/26 |
| 2013/0189721 A1 | * | 7/2013 | Yari ........................ | C12Q 1/26 435/26 |
| 2016/0067272 A1 | * | 3/2016 | El Khal ............... | G01N 33/564 435/26 |

FOREIGN PATENT DOCUMENTS

| | | | | |
|---|---|---|---|---|
| IE | | 42152 B1 * | 6/1980 | |
| WO | WO-2015145387 A1 * | 10/2015 | ........... | G01N 33/492 |

OTHER PUBLICATIONS

Graeff, R and Lee HC, A novel cycling assay for nicotinic acid-adenine dinucleotide phosphate with nanomolar sensitivity. Biochem. J. 2002. 367 (Pt 1): 163-168. (Year: 2002).*

Lowry et al., The stability of pyridine nucleotides. The Journal of Biological Chemistry, vol. 236, No. 10, pp. 2756-2759. 1961 (Year: 1961).*

O'Reilly, T et al. Levels of nicotinamide adenine dinucleotide in extracellular body fluids of pigs may be growth-limiting for Actinobacillus pleuropneumoniae and Haemophilus parasuis. The Canadian Journal of Veterinary Research. 2003. 67: 229-231. (Year: 2003).*

Lilius, E et al. Quantitative extraction and estimation of intracellular nicotinamide nucleotides of *Escherichia coli*. Analytical Biochemistry. 1979. 99: 22-27. (Year: 1979).*

Oyane, A et al. Preparation and assessment of revised simulated body fluids. J. Biomed. Mater. Res. A. 2003. 65(2): 188-195. (Year: 2003).*

Myers, JA et al. Improving accuracy of cell and chromophore concentration measurements using optical density. BMC Biophysics. 2013. 6:4. 15 pages. (Year: 2013).*

Roy, SO et al. NADP-isocitrate dehydrogenase from Pseudomonas nautica: Kinetic constant determination and carbon limitation effects on the pool of intracellular substrates. Applied and Environmental Microbiology. 1998. 64(12): 4958-4964. (Year: 1998).*

Raposo, F et al. Evaluation of analytical calibration based on least-squares linear regression for instrumental techniques: a tutorial review. Trends in Analytical Chemistry. 2016. 77: 167-185. (Year: 2016).*

Zerez, CR et al. Spectrophotometric determination of oxidized and reduced pyridine nucleotides in erythrocytes using a single extraction procedure. Analytical Biochemistry. 1987. 164: 367-373. (Year: 1987).*

(Continued)

*Primary Examiner* — David W Berke-Schlessel
*Assistant Examiner* — Susan E. Fernandez
(74) *Attorney, Agent, or Firm* — Agris & von Natzmer LLP; Joyce V. Natzmer

(57)                    ABSTRACT

Disclosed herein are methods, devices and kits suitable for high throughput screenings of extracellular pyridine nucleotide levels, such as NAD$^+$ levels which are suitable for monitoring pyridine nucleotide induced slowdown of not only pathogenesis of multiple systemic diseases but also aging. In particular, assaying methods quantifying extracellular pyridine nucleotide(s), such as NAD$^+$, in the low micromolar to the low nanomolar range in a sample that may have been subjected to long term storage are disclosed using a two-step enzymatic cycling reaction employing an oxidoreductase such as alcohol dehydrogenase. A modified revised simulated body fluid is also disclosed that is employed as a standard matrix to optimise enzymatic activity, linearity and/or sensitivity of the methods, devices and kits.

31 Claims, 6 Drawing Sheets

(56)            References Cited

OTHER PUBLICATIONS

Bernofsky & Swan, An improved cycling assay for nicotinamide adenine dinucleotide, Anal. Biochem. 53, 452-458 (1973).

Braidy et al., Serum nicotinamide adenine dinucleotide levels through disease course in multiple sclerosis. Brain Research, vol. 1537,pp. 267-272 (2013).

Brunnbauer et al., The nanomolar sensing of nicotinamide adenine dinucleotide in human plasma using a cycling assay in albumin modified simulated body fluids, Nature, Scientific Reports, 8:16110, pp. 1-15 (Oct. 31, 2018).

Glock, G. & Mclean, P., The determination of oxidized and reduced diphosphopyridine nucleotide and triphosphopyridine nucleotide in animal tissues. Biochem J. 61 (3):381-388 (Nov. 1955).

Graeff R and Lee HC, A novel cycling assay for nicotinic acid-adenine dinucleotide phosphate with nanomolar sensitivity. Biochem J. 367 (Pt 1): 163-168 (2002).

Jacobson & Jacobson, Pyridine nucleotide levels as a function of growth in normal and transformed 3T3 cells, Arch. Biochem. Biophys. 175, 627-634 (1976).

Liang, X. et al., Measuring NAD(+) levels in mouse blood and tissue samples via a surrogate matrix approach using LC-MS/MS, Bioanalysis 6(11), 1445-1457 (2014).

Lilius et al., Quantitative extraction and estimation of intracellular nicotinamide nucleotides of *Escherichia coli*, Anal. Biochem. 99, 22-27 (1979).

Lowry et al., The stability of pyridine nucleotides, The Journal of Biological Chemistry, vol. 236, No. 10, pp. 2756-2759 (1961).

Lowry et al., The measurement of pyridine nucleotides by enzymatic cycling, The Journal of Biological Chemistry, vol. 236, 2746-2755 (1961).

Montejano et al., The excited-states quenching of resazurin and resorufin by p-benzoquinones in polar solvents, Dye. Pigment. 64, 117-124 (2005).

O'Reilly & Niven, Levels of nicotinamide adenine dinucleotide in extracellular body fluids of pigs may be growth-limiting for Actinobacillus pleuropneumoniae and Haemophilus parasuis, Can. J. Vet. Res. 67, 229-231 (2003).

Oyane et al., Formation and growth of clusters in conventional and new kinds of simulated body fluids, Journal of Biomedical Materials Research. 64A (2): 339-348 (2003).

Rhodes & Wooltorton, A new fluorometric method for the determination of pyridine nucleotides in plant material and its use in following changes in the pyridine nucleotides during the respiration climacteric in apples, Phytochem. 7, 337-353 (1968).

Slominska et al., Liquid chromatographic/mass spectrometric procedure for measurement of NAD catabolites in human and rat plasma and urine. Nucleosides Nucleotides Nucleic Acids. 25 (9-11):1245-9 (2006).

Trammell et al., Targeted LCMS-based Metabolomics for Quantitative Measurement of NAD+ Metabolites, Comput. Struct. Biotechnol. J. 4, e201301012 (2013).

Woodley & Gupta, New enzyme cycling method for determination of oxidized and reduced nicotinamide adenine dinucleotide, Anal. Biochem. 43, 341-348 (1971).

Zamporlini et al., Novel assay for simultaneous measurement of pyridine mononucleotides synthesizing activities allows dissection of the NAD(+) biosynthetic machinery in mammalian cells. FEBS J. Nov. 2014; 281(22):5104-19 (Epub Oct. 4, 2014.).

Zhu & Rand, A Hydrazine Coupled Cycling Assay Validates the Decrease in Redox Ratio under Starvation in *Drosophila*, PLoS One 7, e47584 (2012).

* cited by examiner

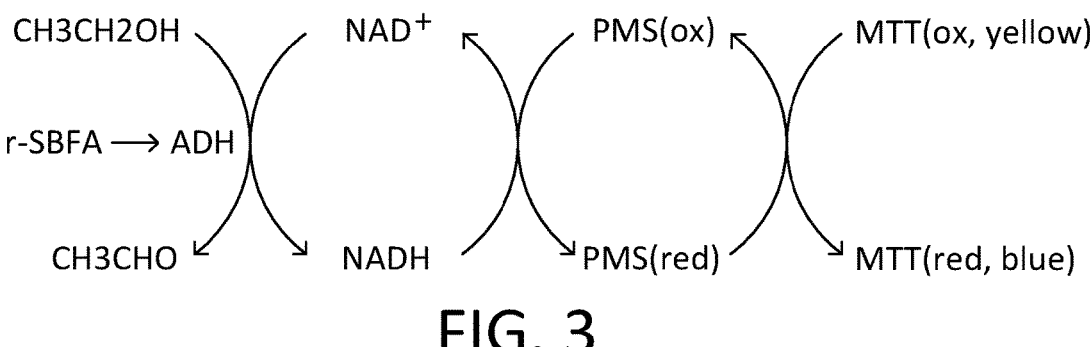
FIG. 3
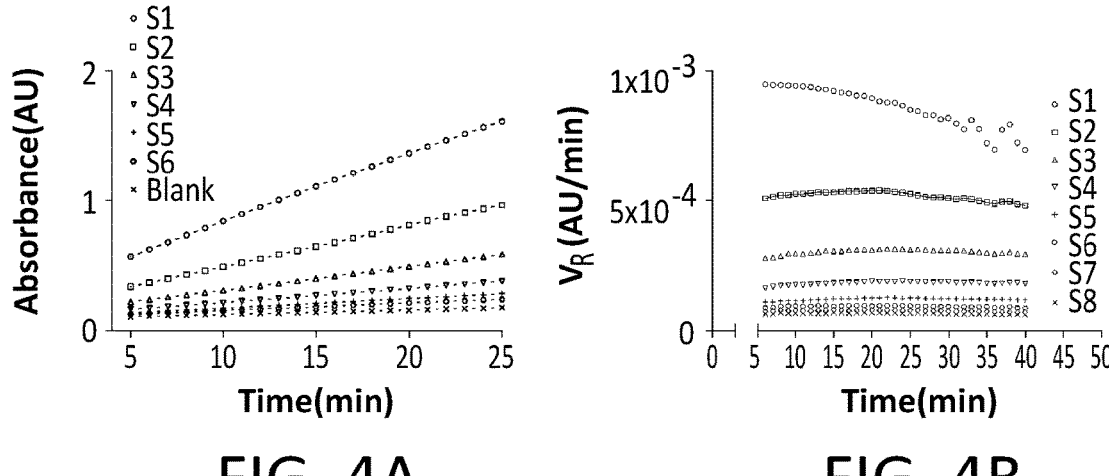
FIG. 4A                                    FIG. 4B
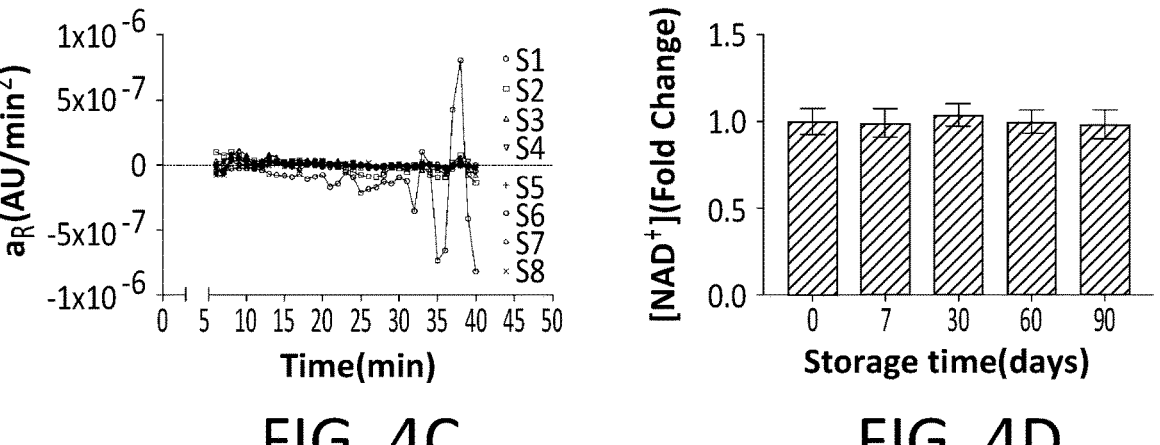
FIG. 4C                                    FIG. 4D

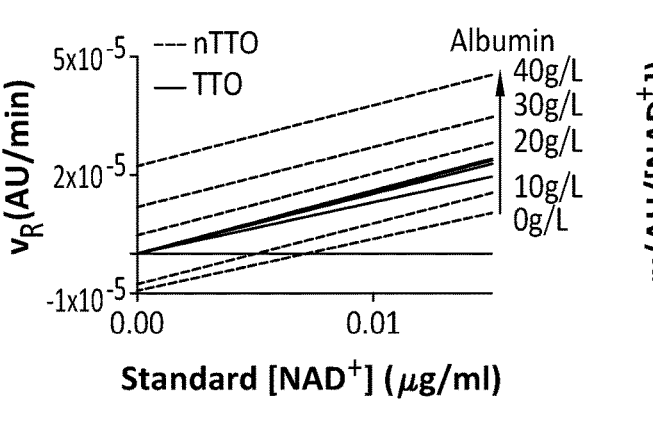
FIG. 6A
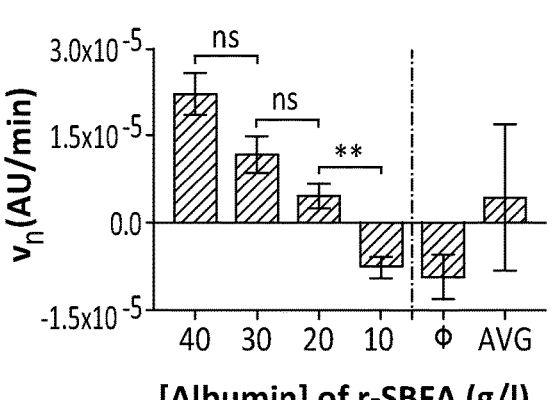
FIG. 6C
FIG. 6B
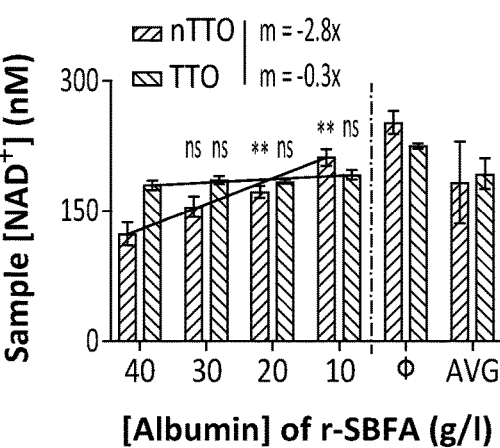
FIG. 6D

METHODS, KITS AND DEVICES FOR MEASURING EXTRACELLULAR PYRIDINE NUCLEOTIDE

CROSS-REFERENCE TO RELATED APPLICATIONS

This application claims the benefit of U.S. provisional application 62/903,111, filed Sep. 20, 2019, which is incorporated herein by reference in its entirety.

BACKGROUND OF THE INVENTION

Nicotinamide adenine dinucleotide (NAD) is a pyridine dinucleotide omnipresent in all living cells either in oxidised (NAD$^+$), or reduced (NADH) form. Its ratio dictates the intracellular redox status and thus determines the overall cellular metabolic state. Extracellular NAD$^+$ (eNAD$^+$) was shown to exhibit, among others, important secondary messenger properties and to induce intracellular calcium release, thereby mediating lymphocyte chemotaxis. Also, eNAD$^+$ is known to be the result of either lytic release from injured tissue or non-lytic release through pore forming proteins like connexin 43 (Cx43) hemichannels and has thus is considered to be involved in the mediation of immune responses and organ function via paracrine signalling.

Any patent, publication, or other disclosure material, in whole or in part, mentioned herein is incorporated herein by reference in its entirety to the extent that the incorporated material does not conflict with definitions, statements, or other disclosure material set forth herein.

Therapeutic applications of eNAD$^+$ have been subject to extensive studies in murine models, with striking findings demonstrating anti-aging, regenerative and highly immunomodulatory effects. For instance, Tullius et al., Nature Communications 5, 1-17 (2014), discovered that the systemic administration of β-NAD$^+$ did not only block autoimmune encephalomyelitis induced paraplegia, but reversed disease progression through remyelination and neuroregeneration. Furthermore, eNAD$^+$ was shown to induce regulatory T cell differentiation, promoting allograft survival in a murine skin transplantation model with implications for concepts of alloimmunity and inflammatory diseases.

However, these findings have so far hardly been translated into medical applications. This can, at least in part, be attributed to the challenges associated with the measurement of extracellular pyridine nucleotides (ePNs), such as eNAD$^+$ in different bodily compartments and the major variations in concentration in those compartments. In human erythrocytes, intracellular NAD$^+$ (iNAD$^+$) was shown to be present at concentrations ranging from 10-40 M, while eNAD$^+$ in pig plasma was found to be present at a fraction of these concentrations, namely 240-290 nM. Appropriate analytical tests thus should be able to reliably measure these vastly different concentration ranges.

High performance liquid chromatography (HPLC) NAD$^+$ analysis methods usually require all samples to be internally spiked with NAD$^+$ and have struggled to quantify NAD due to signal masking and ionisation suppression, especially when followed by ultraviolet-visible (HPLC-UV) spectroscopic quantification (Trammell et al., Comput. Struct. Biotechnol. J. 4, e201301012 (2013)). HPLC methods followed by mass spectrometry (HPLC-MS), and especially tandem mass spectrometry (HPLC-MS/MS), have managed to achieve remarkable sensitivity and specificity for iNAD$^+$ thanks to their ability to separate the respective metabolites through elution with highly specialised columns and successively combining the relaxation time of specific metabolites with their mass spectrum (Liang, X. et al., Bioanal. 6, 1445-1457 (2014)). However, the entirety of the apparatus, namely the columns, the mass or UV spectrometer as well as the actual HPLC machine, required for HPLC analyses, tend to be costly limiting their wide spread use. In addition, typically, each singular measurement of LC-based assays consumes significant amounts of time, from ten minutes up to one hour, making their application for high throughput screenings impractical.

A promising concept enabling the measurement of minuscule analyte concentrations is known as enzymatic cycling, in which a reactant recycling of the analyte takes place and is used to over proportionately amplify a redox indicator dye mediated signal, without the need for additional purification or concentration. First introduced by Warburg et al. in 1935 (Biochem. Z. 282, 157-205 (1935)), the analysis of pyridine nucleotides was pioneered through an enzymatic cycling reaction (Glock, G. & Mclean, P. The Biochem. journal 61, 381-8 (1955); Lowry et al., J. Biol. Chem. 236, 2746-2755 (1961); H., C. P. Eur. J. Biochem. 4, 247-255 (1968). In an effort to refine this method, Rhodes et al., 1968, used alcohol dehydrogenase for the cycling reaction for the quantification of pyridine nucleotides in cox orange apples (Rhodes & Wooltorton, Phytochem. 7, 337-353 (1968)). Although this method relied on the fluorimetric measurement of the highly red fluorescing resorufin, the reduced form of resazurin, the signal might have been masked by the autofluorescence of plasma. In later years, ADH gained popularity and was subsequently adopted as the enzyme of choice, as it is present in all living organisms (Woodley & Gupta, Anal. Biochem. 43, 341-348 (1971); Jacobson, E. & Jacobson, Arch. Biochem. Biophys. 175, 627-634 (1976); Bernofsky & Swan, Anal. Biochem. 53, 452-458 (1973). These studies however focused on iNAD$^+$ rather than eNAD$^+$. See, e.g., U.S. Pat. No. 6,287,796 B1, which is incorporated herein by reference in its entirety.

Thus, there is a need in the art to overcome the challenges of measuring eNAD$^+$ in body fluids such as human plasma. There is furthermore a need to investigate the role of eNAD$^+$ in immunological, oncological and systemic diseases. These and other needs in the art are addressed by the method, devices and kits disclosed herein.

SUMMARY OF THE INVENTION

Various implementations of the methods, devices and kits within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages can become apparent from the description, the drawings, and the claims.

One aspect is directed, among others, at a method for the measurement of oxidized pyridine nucleotides (PNs$^{ox}$) such as extracellular NAD$^+$ (eNAD$^+$) in a body fluid, such as human blood or heparinised plasma produced therefrom. Preferably, the method is standardised, validated and/or optimised for low-cost high throughput screening applications using off-the-shelf materials, including standard laboratory equipment such as microplate readers. In some embodiments, one or more of the methods disclosed herein are designed to investigate in how far PNs$^{ox}$ such as eNAD$^+$ are involved in extracellular paracrine signalling with implications for various systemic diseases. In further embodiments, one or more of the methods disclosed herein facilitate translational research of $PNs^{ox}$ and allow to establish its role in aging and ameliorating aging, respectively as well as the pathogenesis of oncologic or other systemic diseases and ameliorating the same.

In one embodiment, a heat-based pH extraction procedure is disclosed to extract purified versions of primarily oxidized pyridine dinucleotides, such as $NAD^+$, but also, alternatively, reduced pyridine dinucleotides, such as NADH, and subsequently quantifying them, e.g., by a colorimetric two-step enzymatic cycling assay. In a preferred embodiment, the method's sensitivity spans from the low micromolar (μM) to the low nanomolar (nM) range, including less than 5 μM, 4 μM, 3 μM, 2 μM or 1 μM, less than 800 nM, 700 nM, 600 nM or 500 nM, less than 400 nM, 300 nM, 200 nM or 100 nM less than 50 nM, less than 20 nM, but generally more than 5 nM or 10 nMs and uses, in another preferred embodiment, a standard matrix, such as an albumin adjusted revised simulated body fluid (r-SBFA) for heparinised plasma to optimise enzymatic activity and to increase assay linearity. The standard matrix preferably closely resembles the body fluid ultimately tested such as human plasma. The assay preferably satisfies common analytical standards of linearity, reproducibility and/or analyte storage stability.

In one embodiment, a method for determining a concentration of an oxidized extracellular pyridine nucleotide ($ePN^{ox}$), such as oxidized extracellular nicotinamide adenine dinucleotide ($eNAD^+$) in a body fluid of a subject is disclosed. The method comprises:

a) providing the body fluid comprising the $ePN^{ox}$ and reduced extracellular pyridine nucleotide ($ePN^{red}$), such an eNADH, and subjecting the body fluid to an extraction, wherein the extraction removes the $ePN^{red}$ from the body fluid to result in an extracted body fluid comprising $ePN^{ox}$ and none or negligible amounts of $ePN^{red}$, and b) providing more than one pyridine nucleotide standard (PN standard) comprising aliquots of a standard matrix of the body fluid mixed with a known concentration of a pyridine nucleotide which are each subjected or have been subjected to an extraction, wherein the extraction removes the $ePN^{red}$s from the standard to result in an extracted standard comprising $ePN^{ox}$ and none or negligible amounts of $ePN^{red}$, c) providing an oxidoreductase, a substrate of the oxidoreductase and at least one primary and one secondary redox indicator dye to a) and each standard of b) and subjecting each the extracted body fluids and standards, respectively of a) and b) to a cycling process, wherein the cycling process comprises one or more cycles of: the oxidoreductase reducing the $ePN^{ox}$ in a) and each standard of b) to produce $ePN^{red}$, wherein the $ePN^{red}$ donates an electron to the at least one primary redox indicator dye and subsequently to the secondary redox indicator dye resulting in a change of absorbance of the at least one secondary redox indicator dye, d) measuring the change in absorbance in a) and each standard of b) and determining the concentration of the $ePN^{ox}$ in a).

The extraction may comprise removal of corpuscular parts including cells present in the body fluid, preferably without disruption of cell walls in the sample, e.g., by centrifugation at a centrifugal force of between 1500 g to 3500 g, preferably between 2000 g to 3000 g or about 2500 g for 5-30 mins, 10-20 min or about 15 mins at below 25 degrees Celsius, preferably below 20, 15, 10 or 5 degrees Celsius but above 0 degrees Celsius, such as at about 4 degrees Celsius.

The extraction may also comprise providing (i) the body fluid or (ii) the body fluid after removal of corpuscular parts and subjecting (i) or (ii) to acidic conditions to reduce the pH of (i) or (ii) to less than 5, 4, 3, 2 or about 1.5, optionally followed by subjecting (i) or (ii) to an elevated temperature and neutralizing (i) or (ii) to increase the pH to above 6, 7, 8 or about 7.5.

Subjecting (i) or (ii) to acidic conditions may comprise adding an acid solution such as HCl to (i) or (ii). (i) or (ii) may also be subjected to the elevated temperature and the elevated temperature may be a temperature above 50 degrees Celsius including about or above 55, 60, 65, 70, 75 or 80 degrees Celsius. The neutralizing may comprise adding a neutralizing buffer such as mixture of TEA-HCl and KOH.

The subject may have been subject to administration of, e.g., oral and/or intravenous, PN (pyridine nucleotide) supplement for at least 1 week, 2 weeks, 3 weeks, 4 weeks, 2 months, 3 months and more and the concentration of $ePN^{ox}$ may optionally be compared to a base value of $ePN^{ox}$ in the body fluid of the subject prior to administration of the PN supplement.

The oxidoreductase may be a reductase, such as adrenodoxin reductase, aldose reductase or methylenetetrahydrofolate reductase, or a dehydrogenase, such as alcohol dehydrogenase, glucose-6-phosphate dehydrogenase, malate dehydrogenase, lactate dehydrogenase, cytoplasmic isocitrate dehydrogenase, glyceraldehyde-3-phosphate dehydrogenase. or a combination of any one of these reductases or dehydrogenases. In a preferred embodiment, the oxidoreductase is a dehydrogenase, preferably alcohol dehydrogenase (ADH) such as an ADH is from *Saccharomyces cerevisiae*.

The standard matrix may have an optical density that is between 95% and 105% of the optical density of the body fluid; a $pK_a$ value that deviates from the $pK_a$ value of the body fluid by not more than 5, 4, 3, 2 or 1; an ionic composition that corresponds to that of the body fluid in at least one ion, preferably 2 or 3 ions or deviates in the ionic composition of the body fluid for the last least one ion, preferably 2 or 3 ions by not more than 5%; and may further comprise at least one donor of a trace element of an oxidoreductase such as albumin.

The more than one standard may each comprise less than 1000 nM, preferably between 20 nM and 800 nM, of the pyridine nucleotide such as β-NAD. The $pK_a$ value of the standard matrix may be maintained by HEPES (4-(2-hydroxyethyl)-1-piperazineethanesulfonic acid). The oxidized extracellular pyridine nucleotides may be $eNAD^+$ or oxidized extracellular nicotinamide adenine dinucleotide phosphate ($eNADP^+$).

The primary redox indicator dye may be phenazine methosulfate (PMS) and the secondary redox indicator dye may be 3-(4,5-dimethylthiazol-2-yl)-2,5-diphenyltetrazolium bromide (MTT) or a tetrazolium salt thereof.

Aspects are also directed towards kits comprising:
at least one, two, preferably 3, 4, 5 containers each comprising a standard matrix of a body fluid, preferably plasma, saliva or urine, and each comprising a concentration of pyridine nucleotide, such as β-NAD, wherein the concentration of pyridine nucleotide, ranges from 20 nM to 800 nM and includes 40 nM, 60 nM, 80 nM, 100 nM, 150 nM, 200 nM, 250 nM, 300 nM, 350 nM, 400 nM, 450 nM, 500 nM, 550 nM, 600 nM, 650 nM, 700 nM 750 nM and 800 nM;

optionally, an oxidoreductase such as a dehydrogenase such as ADH, preferably ADH from *Saccharomyces cerevisiae*; and a substrate of the oxidoreductase;

optionally, an acid solution such as HCl;

optionally, neutralizing buffer such as mixture of TEA-HCl and KOH; and in a separate container, instructions of how to use the standard matrices to measure eNP$^+$ in a body fluid sample.

Each of the standard matrices may have a pH value of between 7 and 8, preferably between 7.3 and 7.7 and may further comprise, per 1000 ml, between 1-20 g, including 5-15 g, 7-13 g or 10-12 g albumin, preferably serum albumin such as BSA or HSA, and 10-100 g, including 20-80 g, 30-70 g, 35-65 g, 40-50 g or about 40 g of a carrier of a trace element, in particular zinc, such as albumin, such as serum albumin including BSA or HSA. The standard matrices may have the following ionic concentrations in mM: 130-150 Na$^+$, preferably about 142 Na$^+$; 3-6 K$^+$, preferably about 5 K$^+$; 1-3 Mg$^+$, preferably about 1.5 Mg$^+$; 1-4 Ca$^+$, preferably about 2.5 Ca$^+$; 80-180 Cl$^-$, preferably about 100-110 or about 103 Cl$^-$; 2-50 HCO$_3^-$, 20-30, preferably about 27 HCO$_3^-$, 0.5-2 HPO$_4^-$, preferably about 1 HPO$_4^-$, and SO$_4^-$, preferably about 0.5 SO$_4^-$.

One aspect is also directed towards a kit specific for a body fluid comprising:

in one container calibration curves for at least 4, 5 or 6 PN$^{ox}$ standards based on a standard matrix of the body fluid, wherein the PN$^{ox}$ standards are for between 1.5 ng/ml PN$^{ox}$ to 50 ng/ml PN$^{ox}$, such as 1.56, 3.13, 6.25, 12.50, 25.00 and 50 ng/ml PN$^{ox}$, in a second container master mix components comprising components used in the establishment of the calibration curves including at least one oxidoreductase, at least one substrate of the oxidoreductase, a primary redox indicator dye and/or a secondary redox indicator, and instructions how to measure PN$^{ox}$ in the body fluid using the master mix components and calibration curves.

BRIEF DESCRIPTION OF THE FIGURES

FIG. 2A: Comparison of the assay dynamics in different standard matrices utilising the absorbance unit (AU) readings obtained from DEPC water, revised simulated body fluid (r-SBF), revised simulated body fluid adjusted with albumin (r-SBFA) and human plasma, all spiked with 50 µL of 376.8 nM β-NAD standard (S2). FIG. 2B: Fluorescence scan of the autofluorescence of the Master Mix (MM) and a NAD$^+$ sample as prepared in the actual assay reaction, scanned from $\lambda_{ex1}$=280 nm-$\lambda_{ex2}$=850 nm in steps of $\Delta\lambda$=2 nm. The resorufin signal is indicated at $\lambda$=590 nm in the detail view. FIG. 2C: Enzyme dependent assay kinetics for β-NAD standards S1-S6 including a heparinised plasma sample and the blank of a given run using the fluorimetric method. FIG. 2D: Enzyme dependent assay kinetics for β-NAD standards S1-S6 including a heparinised plasma sample and the blank of a given run using the colorimetric method. FIG. 2E: Fluorescence scan of the autofluorescence of the Master Mix (MM) and β-NAD standard S1 as prepared in the actual assay reaction (S1+r-SBFA+MM), scanned from $\lambda_{ex1}$=280 nm-$\lambda_{ex2}$=850 nm in steps of $\Delta\lambda$=2 nm. FIG. 2F: Visual representation of the resorufin quenching effect that occurs when a minuscule amount of heparinised plasma sample is added to the β-NAD standard S1.

FIG. 3. NAD$^+$ cycling principle. Schematic representation of the enzymatic alcohol dehydrogenae (ADH) cycling principle used to measure eNAD$^+$, involving phenazine methosulfate (PMS) as the primary and 3-(4,5-dimethylthiazol-2-yl)-2,5-diphenyltetrazolium bromide (MTT) as the secondary redox indicator dye. The method was inspired by the findings of Rhodes & Wooltorton, Phytochem. 7, 337-353 (1968) and adjusted with insights from the research of Zhu & Rand, PLoS ONE 7, e47584 (2012) and O'Reilly & Niven, Can. J. Vet. Res. 67, 229-231 (2003).

FIGS. 4A-D. NAD$^+$ assay and storage. FIG. 4A: Enzyme dependent assay kinetics for β-NAD standards S1-S6 and the blank of a given run during the assay validation: S1 (753.6 nM), S2 (376.8 nM), S3 (188.4 nM), S4 (94.2 nM), S5 (47.1 nM), S6 (23.5 nM), whilst standards S7 (11.8 nM) and S8 (5.6 nM) were omitted. FIG. 4B: Relative reaction velocities (v$_R$) of standards S1-S8 during min 5-40 of the assay reaction. n=8. FIG. 4C: Relative reaction accelerations (a$_R$) of standards S1-S8 during min 5-40 of the assay reaction. n=8. FIG. 4D: Measured NAD concentrations in human heparinised plasma stored at −80° C. for a given amount of time. No statistical significance was found when comparing the measured timepoints to the baseline (d=0). n=6. Statistics: Two-tailed, unpaired t-test with the confidence limits of CL=99%, as well as a two-way ANOVA (without repeated measures) adjusted with Tukey's multiple comparisons test featuring CL=99%. A significance level of p<0.01 was applied to reject the null hypothesis. All error bars are given in terms of ±SD.

FIG. 5A The ratio of the slope (v$_R$) of two sequential β-NAD standards, (n) and neighbour (n+1), is given by y$_n$ between min 5-25 of the assay reaction. n=8.

FIGS. 6A-6D. Albumin dependency of the assay. FIG. 6A: Comparison of the calibration working curves not through the origin (nTTO, dotted) and to through the origin (TTO, solid) with respect to a varying albumin concentration in the β-NAD standards S1 (753.6 nM) through S6 (23.5 nM) of 0 g/L for the lowermost trace, 10 g/L, 20 g/L, 30 g/L and 40 g/L for the uppermost trace. n=3. FIG. 6B: Comparison of the slopes, m, of the calibration working curves obtained by linear regression analyses nTTO (dark) and to TTO (light) for different albumin concentrations. n=3. FIG. 6C: Variance of the y-axis intercept, v$_n$, of the regression lines nTTO with respect to varying albumin concentrations. n=3. FIG. 6D: Predicted pooled human heparinised sample eNAD$^+$ concentrations using calibration working curves constructed nTTO (dark) and to TTO (light) with respect to varying albumin concentrations. A regression fit over the physiological range of albumin concentrations yielded y=−2.84xnML/g+236.5 nM (R$^2$=0.9785) for the nTTO and y'=−0.34xnML/g+194 nM (R$^2$=0.7706) for the TTO approach. n=3. Statistics: Two-tailed, unpaired t-test with the confidence limits of CL=99%, where a significance level of p<0.01 was applied to reject the null hypothesis. **p<0.01. All error bars are given in terms of ±SD. The dotted line represents the physiological range of albumin concentrations.

FIG. 7A: Mean relative reaction velocities ($v_R$) for β-NAD standards S1 (753.6 nM) through S8 (5.6 nM) and the blank (B) measured between min 5-25 of the assay reaction. n=8. FIG. 7B: The ratio ($\varepsilon_n$) of standard deviations ($\sigma_n$), to the difference in relative reaction velocity ($v_R$) of two sequential β-NAD standards, (n) and neighbour (n+1), represented by $\psi_n$. n=8. FIG. 7C: Calibration working curve constructed from the average slopes ($v_R$) of β-NAD standards S1 (753.6 nM) through S6 (23.5 nM), obtained from the eight-fold assay repetition. n=8. FIG. 7D: Blood samples were taken from patients scheduled to undergo hernioplasty and analysed for their eNAD$^+$ concentration. Statistics: n=10. Among the analysed, there were 8 male and 2 female patients, where the mean age averaged (52.1±15.8) years, ranging from 29 to 75 years. The underlying diseases were inguinal hernia (n=7), epigastric hernia (n=1), hiatal hernia (n=1) and umbilical hernia (n=1). The overall average is displayed. Statistics: Two-way ANOVA (without repeated measures) adjusted with Tukey's multiple comparisons test with CL=99%. A significance level of p<0.01 was applied to reject the null hypothesis. ****p<0.0001. All error bars are given in terms of ±SD.

DETAILED DESCRIPTION OF VARIOUS AND PREFERRED EMBODIMENTS

Figure 1:
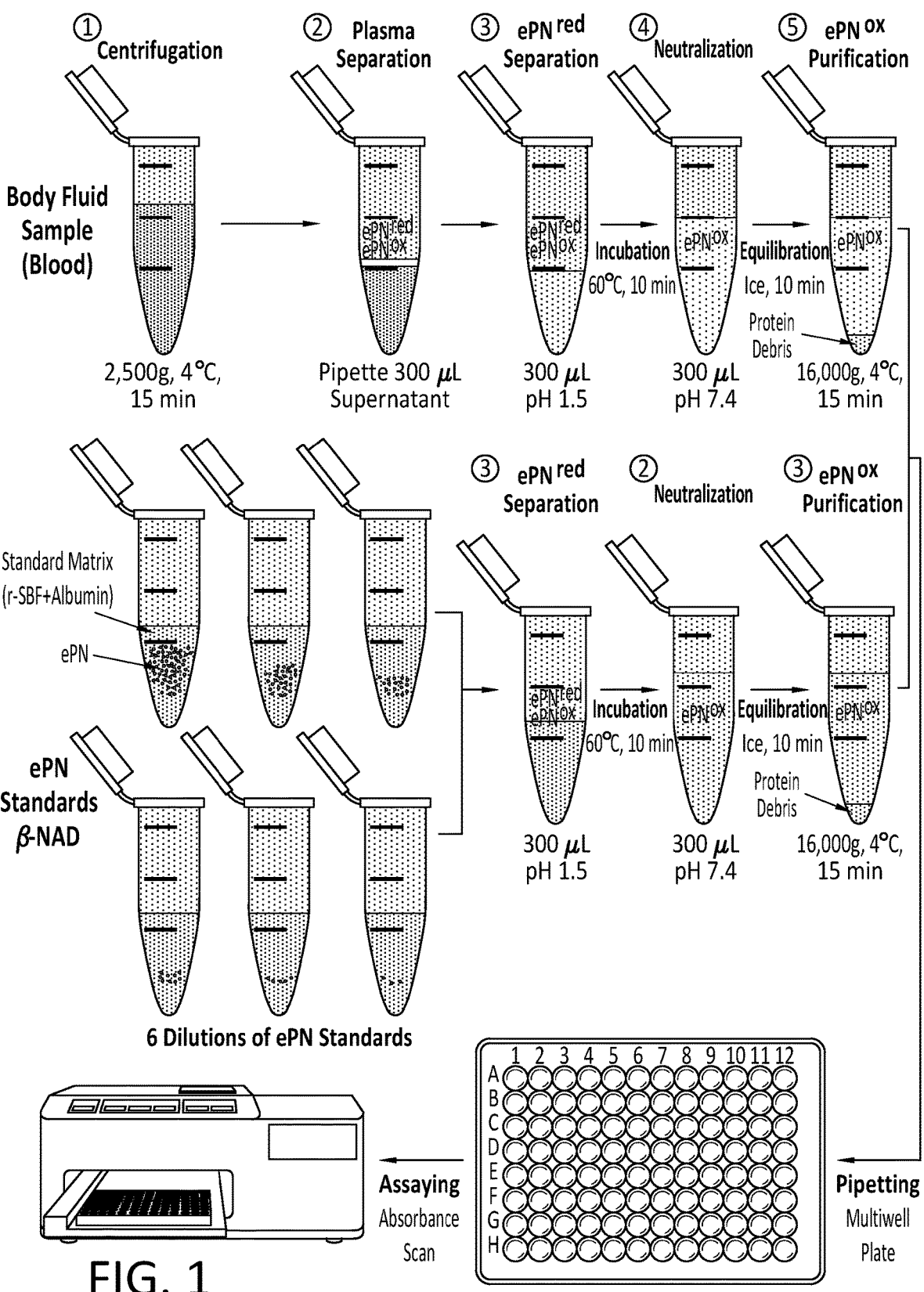
FIG. 1: Flowchart of the PN$^{ox}$ extraction and subsequent assaying of the purified PN$^{ox}$. The PN$^{red}$ removal and PN$^{ox}$ neutralization buffers were prepared in as buffer (DEPC (Sigma, USA, Catalog No: D5758) water). The PN$^{red}$ removal buffer consisted of a 0.3N HCl solution and the neutralization buffer comprised equal parts of 0.36N TEA-HCl (ACROS, USA, Catalog No: 170051000) and 0.6N KOH. The preparation of a standard against which the body fluid sample is compared is also shown.

The definitions herein are provided to aid in describing particular embodiments and are not intended to limit the claimed invention. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

Body fluids according to the present inventions include, but are not limited to saliva, urine, lymph, whole blood, anticoagulated whole blood, serum, preferably plasma, e.g. heparinized plasma (e.g. produced via heparin tubes that are coated on the inner surface with sodium heparin or lithium heparin such as VACUETTE® heparin tubes). In certain embodiments the body fluid is free or has been freed of inhibitors of the oxidoreductase used, e.g., chelating agents such as EDTA that inhibits ADH. In certain embodiments the body fluid has been frozen for more than an hour, 12 hours, a day, two, three, four, five, six, seven, eight, nine, ten, eleven, twelve, thirteen days, two, three, four, five, six, seven weeks or two, three, four, five or six months. In some embodiments, the sample is a heparinized plasma sample from a mammal such as a human, which is preferably free or substantially free of an oxidoreductase-inhibiting such as ADH-inhibiting chelating agent and which has optionally been frozen as outlined above. The freezing temperature might be up to −90 degrees Celsius or lower or, in other embodiments, higher, such as −80, −70, −60, −50-, 40, −30 or −20 degrees Celsius. The sample might be frozen for storage via, e.g., liquid nitrogen.

Pyridine nucleotides (PNs) are molecules comprising two mononucleotides, adenosine monophosphate (AMP) and nicotinamide mononucleotide (NMN). They exist as oxidized and reduced nicotinamide adenine dinucleotides in their unphosphorylated (NAD$^+$ or NADH) and phosphorylated (NADP$^+$ or NADPH) forms, which are collectively referred to herein as PN$^{ox}$ and PN$^{red}$, respectively. PNs are soluble coenzymes of oxidoreductases and undergo reversible oxidation and reduction in several biological electron-transfer reactions.

Intracellular pyridine nucleotides (iPNs) are PNs that are present within a cell. To isolate them, the cell walls have to be made permeable/broken up such as described, for example, in U.S. Pat. No. 6,287,796 B1, which is incorporated herein by reference in its entirety.

Extracellular pyridine nucleotides (ePNs) are PNs that are present in body fluids outside the cell. A certain level of ePNs exists in an organism's blood and may or may not be increased by supplements, with might be administered, e.g., orally, intravenously or subcutaneously. Many supplements, including dietary supplements, contain, e.g., in particular NAD$^+$ precursors such as nicotinic acid (NA), nicotinamide riboside (NR), nicotinamide (Nam), Nicotinic Acid Mononucleotide (NaMN), Nicotinic Acid Adenine Dinucleotide (NaAD), Quinolinic Acid (QA), Aspartic Acid (Asp) and/or Tryptophan (Trp). Supplements, that are aimed at increasing the ePN content of a body fluid of an organism to whom the supplement(s) was provided are collectively referred to herein as PN supplements. Such PN supplements may be part of a drug/medication. The present invention is, in certain embodiments, directed at assessing in how far such supplements effectively increase the concentration of ePNs and thus confer the beneficial properties associated with higher levels of ePNs in an organisms (human and non-human) blood. According to the invention ePNs at concentration lower than 1000 nM, lower than 900 nM, lower than 800 nM, lower than 700 nM, lower than 600 nM, lower than 500 nM, lower than 400 nM, lower than 300 nM, lower than 200 nM, lower than 100 nM, lower than 50 nM, lower than 40 nM, lower than 30 nM, lower than 20 nM, lower than 10 nM, including, e.g., above 1 nM but below 100 nM can be measured.

Extraction

When assessing ePNs concentrations in particular in whole blood, care has to be taken that iPNs are not released from any cells contained in the whole blood. Thus, in a preferred embodiment, corpuscular parts including cells are removed from, e.g., whole blood by centrifugation at between by centrifugation at a centrifugal force of between 1500 g to 3500 g, preferably 2000 g to 3000 g or about 2500 g for 5-30 mins, 10-20 min or about 15 mins at below 25 degrees Celsius, preferably below 20, 15, 10 or 5 degrees Celsius but above 0 degrees Celsius, such as at about 4 degrees Celsius. Prior to any separation cell walls should be kept intact so that the extracted material is substantially free of iPNs and active tissue and/or cell wall disruption (lysis), either by chemical or mechanical means should be omitted. After removal of any corpuscular parts, the remaining serum can be transferred to a separate tube, which in certain embodiments contains anticoagulant and the resulting plasma can be processed as described herein. A sample, which may be a body fluid such as plasma, is considered to be substantially free of/comprise substantially no iPNs if the iPNs constitute are less than 2%, preferably less than 1% of the total amount of PNs are iPNs.

The extraction removes the ePN$^{red}$ from a sample to result in an extracted body fluid comprising ePN$^{ox}$ and none or negligible amounts of ePN$^{red}$. The amount of ePN$^{red}$ is considered negligible if the ePN$^{red}$ constitutes less than 2%, preferably less than 1% of the total amount of ePNs and vice versa that is then subjected to the cycling reaction described herein.

The measured ePNs are, as discussed elsewhere, generally present in considerably lower concentrations than intracellular pyridine nucleotides (iPNs). To obtain an extracted body fluid that maintains all $ePN^{ox}$ contained in the body fluid but contains none or negligible amounts of $ePN^{red}$, the body fluid is subjected to acidic conditions, preferably highly acidic conditions, e.g. by adding an acid solution such as HCl, to an aliquot of the body fluid (e.g. heparinized plasma), to reduce the pH of the plasma to a pH of less than 5, 4, 3, 2, preferably to less than 3, 2 or about 1.5. After an incubation under conditions designed to destroy $ePN^{red}$, such as more than 40 degrees Celsius, preferably more than 50 degrees Celsius, more than 55, 60, 65, 70, 75, or 80 degrees Celsius or about 60 degrees Celsius, the sample is neutralized by, e.g., adding a neutralization buffer such as a mixture of TEA-HCl and KOH. The latter shifts the pH of the sample back to a pH above 6, 7, 8 or around 7.5 and/or into the working range of an oxidoreductase, preferably one later used to reduce the $ePN^{ox}$. In a preferred embodiment, the extraction takes less than 4 hours, less than 3 hours, less than 2 hours, 60, 50, 40 or 30 minutes or less. The extraction can be accelerated, by e.g. increasing the extraction temperatures discussed above to temperatures above 60, 70 or 80 degrees Celsius.

The oxidoreductase used to reduce the $ePN^{ox}$ and vice versa is preferably a dehydrogenase, preferably alcohol dehydrogenase (ADH), e.g., ADH from *Saccharomyces cerevisiae*. Other oxidoreductases include, but are not limited to reductases, such as adrenodoxin reductase, aldose reductase or methylenetetrahydrofolate reductase, other dehydrogenases, such as glucose-6-phosphate dehydrogenase, malate dehydrogenase, lactate dehydrogenase, cytoplasmic isocitrate dehydrogenase, glyceraldehyde-3-phosphate dehydrogenase. or a combination of any one of these reductases or dehydrogenases. Any alcohol dehydrogenase or aldehyde reductase that catalyzes the reaction:

primary alcohol+NAD($^+$) $\leftrightarrows$ an aldehyde+NADH; and/or secondary alcohol+NAD($^+$) $\leftrightarrows$ a ketone+NADH; and/or alcohol+NADP($^+$) $\leftrightarrows$ an aldehyde+NADPH; and/or alcohol+NADP($^+$) $\leftrightarrows$ an aldehyde+NADPH and uses $Zn^{2+}$ or Fe cation(s) as trace elements (see EC 1.1.1.1, and EC1.1.1.2, revised as of Nov. 29, 2018, which are incorporated herein by reference in their entirety) are within the scope of the present invention.

A standard matrix is a liquid that resembles the body fluid tested in at least the optical density and buffering capacity ($pK_a$ value). In certain embodiments, the standard matrix also resembles the body fluid tested in ionic concentration and/or protein concentration. The standard matrix also contains, if required for the oxidoreductase's activity, trace elements, preferably donors for trace elements required by the oxidoreductase used. The standard matrix for blood plasma in a method in which the oxidized extracellular pyridine nucleotide is reduced via ADH, may, for example, be a revised simulated body fluid adjusted with albumin (r-SBFA) as, e.g., described in detail elsewhere herein. HEPES may provide the appropriate buffering capacity (pKa value); albumin may be the source of a trace element, such as zinc, required for the function of the oxidoreductase, e.g., ADH. In certain embodiments the albumin provides the zinc over time in the amounts required for the ADH's activity, for example to reduce oxidized extracellular pyridine nucleotides. In a particularly preferred embodiment, the standard matrix is a solution with an ion concentration close to that of the body fluid such as human blood plasma. In certain embodiments the invention employs or is directed to a standard matrix which has a pH between 6 and 9, preferably between 7 and 8, between 7.2 and 7.8 or around 7.5. In certain preferred embodiments the standard matrix has:

an optical density that is between 95% and 105% of the optical density of the body fluid;

a $pK_a$ value that deviates from the $pK_a$ value of the body fluid by not more than 5, 4, 3, 2 or 1; and/or an ionic composition that corresponds to that of the body fluid in at least one ion, preferably 2 or 3 ions or deviates in the ionic composition of the body fluid for the last least one ion, preferably 2 or 3 ions by not more than 5%.

TABLE 1 shows an ionic concentration of human blood plasma and under 5 the ionic concentration (nM) of an example of a standard matrix of the present invention referred to herein as r-SBF. As the person skilled in the art will readily recognize deviations from the values shown, by 5% or 10% are within the scope of the present invention. Oyane et al., *Journal of Biomedical Materials Research.* 64A (2): 339-348 (2003).

Ionic concentrations (nM) of blood plasma and proposed SBF formulations

| | Formulation | Na$^+$ | K$^+$ | Mg$^{2+}$ | Ca$^+$ | Cl$^-$ | HCO$_3^-$ | HPO$_4^{2-}$ | SO$_4^{2-}$ | Buffer |
|---|---|---|---|---|---|---|---|---|---|---|
| 0 | Blood Plasma | 142.0 | 5.0 | 1.5 | 2.5 | 103.0 | 27.0 | 1.0 | 0.5 | |
| 1 | Original SBF | 142.0 | 5.0 | 1.5 | 2.5 | 148.8 | 4.2 | 1.0 | 0.0 | Tris |
| 2 | Corrected (c-SBF) | 142.0 | 5.0 | 1.5 | 2.5 | 147.8 | 4.2 | 1.0 | 0.5 | Tris |
| 3 | Tas-SBF | 142.0 | 5.0 | 1.5 | 2.5 | 125.0 | 27.0 | 1.0 | 0.5 | Tris |
| 4 | Bigi-SBF | 141.5 | 5.0 | 1.5 | 2.5 | 124.5 | 27.0 | 1.0 | 0.5 | HEPES |
| 5 | Revised (r-SBF) | 142.0 | 5.0 | 1.5 | 2.5 | 103.0 | 27.0 | 1.0 | 0.5 | HEPES |
| 6 | Modified (m-SBF) | 142.0 | 5.0 | 1.5 | 2.5 | 103.0 | 10.0 | 1.0 | 0.5 | HEPES |
| 7 | Ionized (i-SBF) | 142.0 | 5.0 | 1.0 | 1.6 | 103.0 | 27.0 | 1.0 | 0.5 | HEPES |
| 8 | Improved (n-SBF) | 142.0 | 5.0 | 1.5 | 2.5 | 103.0 | 4.2 | 1.0 | 0.5 | Tris |

The standard matrix contains, in certain instances, specific amounts of pyridine nucleotide, such as β-NAD, $C_{21}H_{27}N_7O_{14}P_2 \cdot xH_2O$, Molecular Weight: 663.43 (anhydrous basis). These amounts are added to e.g. the r-SBF which is, prior to the addition, free of pyridine nucleotides. The amount of pyridine nucleotide added may range from 10 nM to 1000 nM or 20 nM to 800 nM and includes 40 nM, 60 nM, 80 nM, 100 nM, 150 nM, 200 nM, 250 nM, 300 nM, 350 nM, 400 nM, 450 nM, 500 nM, 550 nM, 600 nM, 650 nM, 700 nM 750 nM and 800 nM. The resulting standard matrices containing these specific amounts of PNs, are also referred to herein as PN standard(s).

Cycling Reaction

In one step of the cycling reaction, pyridine nucleotide is reduced. Reduction may be performed by adding an enzyme and enzyme substrate pair to the extracted body fluid. For the measurement of $ePN^{ox}$, the oxidoreductase and its substrate, as described above, are added. In a preferred embodiment, the substrate is provided in excess, which means at a concentration of more than 0.3, 0.4 or 0.5 M, such as 0.5 M to 1 M or 0.5 M to 2 M. Any oxidoreductase and its substrate capable of reducing NAD and NADP may be used. Such pairs may include artificial or genetically engineered enzymes and substrates. As a result of the reduction, the $ePN^{ox}$ present is converted to $ePN^{red}$.

In the second step of the cycling reaction, an electron is transferred from the $ePN^{red}$ to a primary and subsequently to a secondary redox indicator dye. Preferred primary redox indicator dyes, include, but are not limited to, oxidized phenazine ethosulfate ($PES^{ox}$), oxidized phenazine methosulfate ($PMES^{ox}$), 5-methylphenazinium methylsulfate, 1-methoxy-5-methylphenazinium methylsulfate, diaphorase (dihydrolipoamide reductase, EC 1.6.4.3.) or a combination of these compounds. In the transfer reaction, the electron from NADH or NADPH is first transferred to the primary redox indicator dye, and from there to the secondary redox indicator dye.

During the second step of the cycling reaction, the $ePN^{red}$ is oxidized again to $ePN^{ox}$. The $ePN^{ox}$ may then serve as substrate for the first step of the cycling reaction, i.e., the reduction of pyridine nucleotide. The cycle may be repeated many times to generate a detectable signal from a small concentration of $ePN^{ox}$.

The secondary redox indicator dye may be any dye molecule that shows a detectable absorbance change after acceptance of an electron. Preferred electron acceptor dyes include, but are not limited to, thiazolyl blue (MTT), 3,3'-(3,3'-dimethoxy-4,4'-biphenylene)-bis(2-(p-nitrophenyl)-2H-tetrazolium chloride) (NBT), 3-(p-indophenyl)-2-(p-nitrophenyl)-5-phenyl-2H-tetrazolium chloride (INT), 3,3'-(4,4'-biphenylene)-bis(2,5-diphenyl-2H-tetrazoliumchloride), 3,3'-(3,3'-dimethoxy-4,4'-biphenylene)-bis(2,5-diphenyl-2H-tetrazolium chloride), 3,3'-(3,3'-bis(2,5-bis(p-nitrophenyl)-2H-tetrazolium chloride) and a combination of these dyes.

A master mix (MM) as used herein contains apart from $PN^{ox}$ and the standard matrix all the molecules required for the cycling reaction including the oxidoreductase and its substrate, primary and a secondary redox indicator dye and a buffer such as diethyl decarbonate.

Absorbance scans may be performed with any appropriate device such as a microplate reader, such as a reader for 96 well plates such as at e.g., between $\lambda ex1=200-\lambda_{ex2}=900$ nm, $\lambda_{ex1}=280-\lambda_{ex2}=850$ nm, $\lambda_{ex1}=400-\lambda_{ex2}=800$ nm, $\lambda_{ex1}=500-\lambda_{ex2}=700$ nm. The absorbance change of the secondary redox indicator dye is then measured at the appropriate wavelength. For e.g. MTT, an appropriate wavelength is 565 nm is appropriate.

In one example, the body fluid is saliva and is tested for $eNAD^+$. Relative to FIG. 1, centrifugation and separation are omitted. The eNADH is removed by adding a buffer that lowers the pH of the saliva to a pH of less than 2. The eNADH is destroyed by incubation of the mix at 80° C. for 5-10 min. Subsequently, the mix is neutralized by adding a neuralization buffer to increase the pH to above pH 7. The resulting mix is centrifuged to remove any protein debris and loaded onto a multiwell plate. The respective standard matrix for saliva containing 50.00, 25.00, 12.50, 6.25, 3.13 and 1.56 β-NAD+ (ng/mL) S1-S6, are provided. A two-step cycling reaction using $PES^{ox}$, NBT and methylenetetrahydrofolate reductase and methylenetetrahydrofolate is performed and the emission spectra is measured at a wavelength between 550 and 610 nm.

In another example, the body fluid is urine and is tested for $eNADP^+$. Relative to FIG. 1, centrifugation and separation are omitted. The eNADPH is removed by adding a buffer that lowers the pH of the saliva to a pH of less than 1.5. The eNADPH is destroyed by incubation of the mix at 70° C. for 8 min. Subsequently, the mix is neutralized by adding a neuralization buffer to increase the pH to above pH 7.3. The resulting mix is centrifuged to remove any protein debris. The respective standard matrix for urine containing 50.00, 25.00, 12.50, 6.25, 3.13 and 1.56 βNADP+ (ng/mL) S1-S6, are provided. A colorimetric two-step enzymatic cycling assay to eNADP+, such as cycling reaction with the master mix containing $PMES^{ox}$, INT, lactate dehydrogenase and lactate is performed and the emission spectra is measured at a wavelength between 550 and 610 nm.

In a preferred embodiment, $eNAD^+$ in human heparinised plasma was assayed in, e.g., a clinical setting. Here, the whole blood sample was centrifuges and shown in FIG. 1, which was followed by the sequence of steps shown in this Figure. An albumin modified r-SBF was used to ensure physiological enzymatic activity. In addition, assay linearity and reproducibility and long-term storage stability of, e.g., $eNAD^+$ in frozen human heparinised plasma was established. In order to validly calculate $PN^{ox}$ levels in, e.g., $eNAD^+$ levels in human plasma, an appropriate and in vivo-like standard matrix was established. The assay quantified $eNAD^+$ via a two-step enzymatic cycling reaction, based on an oxidoreductase such as ADH (FIG. 3).

Physiologically speaking, albumin is the most abundant plasma protein, with a concentration generally in the range of 35 g/L-50 g/L, whilst being the main carrier of zinc in blood, as approximately 80% of all plasma zinc is bound to albumin. Thus, it serves as a major zinc donor in blood, comprising part of the so-called exchangeable pool, which, given zinc's role as a blood trace element, is important to the proper functioning of ADH. In fact, a catalytic zinc ion binds to ADH's Cys-43, Cys-153 and His-66 amino acid residues. Thus, in one embodiment of the invention, albumin was added to r-SBF, providing for a potent zinc donor in r-SBF, or, e.g. in DEPC, both of which do not contain zinc. The deviation from linearity after about 30 min in all zinc-free matrices, indicating a decreased ADH reaction speed and successive plateauing substrate conversion rate, might in fact result from zinc deprivation. However, this was alleviated through the addition of 40 g/L of albumin to r-SBF, as demonstrated in FIG. 2. Indeed, it was hypothesized that, under the assumption that albumin's affinity for zinc is not infinitely large, some of these zinc ions will be competed for, and eventually be seized by ADH. In addition, the extreme pH milieus, combined with the heat incubation during $PN^{ox}$ extraction, may cause a release of zinc from albumin, facilitated by its denaturation. Results obtained from the comparison of different standard matrices, presented in FIG. 2A, seem to corroborate this hypothesis, for r-SBFA replicated the assay kinetics observed in human heparin plasma almost indiscriminately.

Moving on to the analyte isolation, a heat based dichotomous pH extraction procedure was utilised to extract and amass purified versions of either $NAD^+$ at pH 1.5, as can be seen in FIG. 1, in consideration of Lowry, J. Biol. Chem. 236, 2746-2755 (1961) and Lilius et al. Anal. Biochem. 99, 22-27 (1979).

As the assaying method was intended to quantify $eNAD^+$ plasma levels in exploratory studies, storage stability of eNAD in human heparinised plasma at $-80°$ C. was tested as there was the possibility that $eNAD^+$ would be hydrolysed by ectoenzymes from the family of NADases such as CD38 or ADPribosyltransferases like ART. The stability of $eNAD^+$ in frozen human plasma for at least three months was confirmed, which was in accordance with a murine study that demonstrated its stability for at least one week, as well as the known stability of $\beta$-NAD in aqueous solution for at least six months.

With respect to the fluorimetric evaluation as an alternative quantification method, some potentially detrimental properties of human blood plasma that may hinder the measurement of $eNAD^+$ using resazurin were considered. First and foremost, naturally occurring porphyrins cause the autofluorescence of human blood plasma to exhibit two prominent spikes at 630 nm and 590 nm, of which the latter one happens to be at the exact frequency resorufin fluorescence. It is further known that these autofluorescence spectra can vary substantially over the range of 500-600 nm, due to immense variations in plasma porphyrin levels, which are common, e.g., in patients with cancer. What is more, another biological molecule with a broad autofluorescence band around 500-600 nm is bilirubin. The vast fluctuations in bilirubin levels, especially in patients suffering from liver disease can therefore cause significant baseline shifts that are very difficult to correct for. Having used resazurin instead of MTT, it became apparent that there was an almost complete eradication of the signal in plasma, while the standards remained readily quantifiable. Moreover, the impact of adding a small amount of a plasma sample to the first $\beta$-NAD standard, S1, was tested which resulted in a sharp drop in the signal, clearly demonstrated in FIGS. 2E and 2F. Besides the aforementioned reasons, a few possible explanations are herein presented that could be responsible for this apparent quenching of the resorufin signal at the 590 nm emission band. In fact, Montejano, et al., Dye. Pigment. 64, 117-124 (2005) described that resorufin is quenched by quinones at this very frequency band. Given the endogenous nature of these molecules, the sharp drop in resorufin's fluorescence upon the addition of a small plasma quantity (which even contained physiological $eNAD^+$ concentration) supports this hypothesis and explains why $eNAD^+$ is not measurable in a full plasma sample via fluorescence spectroscopy.

In comparison to other measuring procedures of PNs such as $NAD^+$, $eNAD^+$ has been studied to a far lesser extent than $iNAD^+$, most likely due to its drastically lower concentrations of 240-290 nM for extracellularly (ePNs), relative to concentrations from 10-40 M for intracellularly pyridine nucleotides (iPNs), which presents nontrivial analytical challenges. Alternative to the quantification of chromogenic or fluorescent signals, the concentration of $iNAD^+$ has been measured using a multitude of sophisticated high-performance liquid chromatography (HPLC) methods such as HPLC-UV, as well as HPCL-NMR, while, in a more specialised scenario, HPLC-UV and HPLC-MS have been employed to evaluate murine erythrocyte intracellular $NAD^+$ ($iNAD^+$) levels. These methods have been used predominantly to measure $iNAD^+$, and only very few could be at least theoretically been used to study $eNAD^+$ directly without any preceding concentrating steps, for their relatively high limit of quantification. However, Liang et al., 2014 used a modified version of the HPLC-MS, namely the electrospray ionisation HPLC-ESI-MS to successfully measure $eNAD^+$ in murine blood (Liang, X. et al., Bioanal. 6, 1445-1457 (2014)). Nonetheless, for all analytical methods involving calibration methods, the standard matrix should exhibit comparable traits to the biological sample matrix and should either be a laboratory prepared or analyte-stripped version of the matrix of interest. In fact, Liang et al., 2014 used HPLC grade water in their HPLC-ESI-MS analysis, which seemed to be common practice amongst other HPLC based analyses. This opens up the analysis of $NAD^+$ to be subject to significant signal distortions through imperfect enzyme kinetics, signal masking by other analytes or by ionisation suppression. In addition, the apparatus required for HPLC analyses tends to be rather expensive, therefore limiting their availability to the general scientific community, whereas the enzymatic cycling method used herein merely required an ordinary microplate reader, present in virtually all laboratories by default, in addition to any kind of transparent 96 well plate.

When it comes to plasma compounds that could affect the assays performance, it was evaluated whether the oxidoreductase such as ADH is the main source of measurement variation, as it represents the main rate limiting factor in the redox dye conversion reaction. For instance, human isoforms of ADH are generally inhibited by common drugs such as aspirin or H2 receptor blockers in the form of cimetidine or ranitidine. These drugs might be present in the plasma of individual patients at distinct concentrations. What is more, these drugs might very well resist, in part, the extraction, neutralisation and deproteinisation steps, thereby modulating the activity of ADH in the assay reaction. This could cause $eNAD^+$ measurement variations at an inter- as well as intrapatient levels. ADH is characterised further through a modulatory effect by different hormones, such as growth hormones, epinephrine or estrogens which act in a stimulatory manner, while thyroid hormones and androgens can inhibit ADH's activity. Therefore, varying baseline levels of these hormones upon blood collection could further impact the behavior of ADH in the plasma sample. However, this assumption seems to be more theoretical as due to the elevated temperatures during extraction (e.g., $60°$ C. heat incubation for 10 min at pH 1.5) will denature virtually all proteins and hormones. It is well known that ADH features broad specificity to aliphatic alcohols other than ethanol. For instance, it oxidises methanol to produce formaldehyde. In fact, methanol is of varying concentration is present in human blood, partly due to dietary preferences for artificial sweeteners such as aspartame. Fasting blood levels of methanol were found to be on average 168 μmol/L, which corresponds to 5.39 mg/dL. However, the assay procedure will cause a 6-fold dilution of methanol levels, yielding an approximate concentration 1 mg/dL, which is less than 1% of the ethanol concentration in the MM (being 125 mg/dL). Furthermore, ADH can also metabolise retinol (Vitamin A), which is often present in blood plasma at levels around 60 μg/dL. It is due to the fact that ethanol's concentration, as key substrate of ADH in the MM, was chosen to lie well beyond the point of saturation, that neither methanol nor retinol are expected to have a prominent effect on the measured eNAD$^+$, for their minuscule concentrations. In sum, it was hypothesized that hormones, proteins and vitamins endogenous to human blood, will produce merely negligible effects on the assay, thanks to the extraction as illustrated, e.g. in FIG. 1, which provides a harsh environment that most of these compounds cannot withstand.

Blood Collection Method and Concentration of Oxidoreductase and its Substrate

Lithium heparin tubes were used for the collection of blood samples as the common chelating agent K3EDTA is in fact a potential potent inhibitor of ADH as used herein, and could therefore eradicate linear enzyme behavior. To ensure optimal enzyme activity, the concentrations of the oxidoreductase and its substrate (e.g. ADH and ethanol), are preferably chosen to be well beyond their point of saturation, so that any effect of even an ever so slight variation in their respective amounts would be essentially nullified.

Evaluation of the Standard Matrix and Spectroscopy Method

A standard matrix as described herein aims at matching the enzymatic cycling behavior in, e.g., plasma. To match the enzyme kinetics of, e.g., ADH in human heparinised plasma and to provide the required sensitivity for the assay, several standard matrices were compared against human plasma. The standard matrices tested, included DEPC water, r-SBF and r-SBFA and used β-NAD. Since a standard matrix might not be completely free of analyte, and, since, e.g., human plasma endogenously contains eNAD$^+$, every standard matrix was accompanied by blanks produced from the same matrix. The resulting absorbance unit (AU) readings are presented in FIG. 2A, where all matrices tested were spiked with 50 μL of β-NAD standard S2 (376.8 nM). A qualitative inspection revealed that r-SBFA and heparinised plasma both showed a highly linear increase, while DEPC and r-SBF did not. The absorbance increase reflects the enzyme velocity of ADH, and was highest in human heparinised plasma, with an increase of approximately 1.95 AU over the course of 60 min and 1.84 AU for the runner up, r-SBFA, trailed by 1.27 AU and 1.07 AU for DEPC and r-SBF, respectively. Analogously, the relative reaction velocity, $v_R$, in plasma and r-SBFA were of remarkable resemblance, namely $v_{RP}$=0.0317±0.0002 and $v_{RA}$=0.0306±0.0002, respectively. All things considered, r-SBFA was found to most closely resemble the in vivo enzyme kinetics of ADH and was therefore adopted as the standard matrix in the following experiments.

Figures 2A, 2B, 2C, 2D, 2E, 2F:
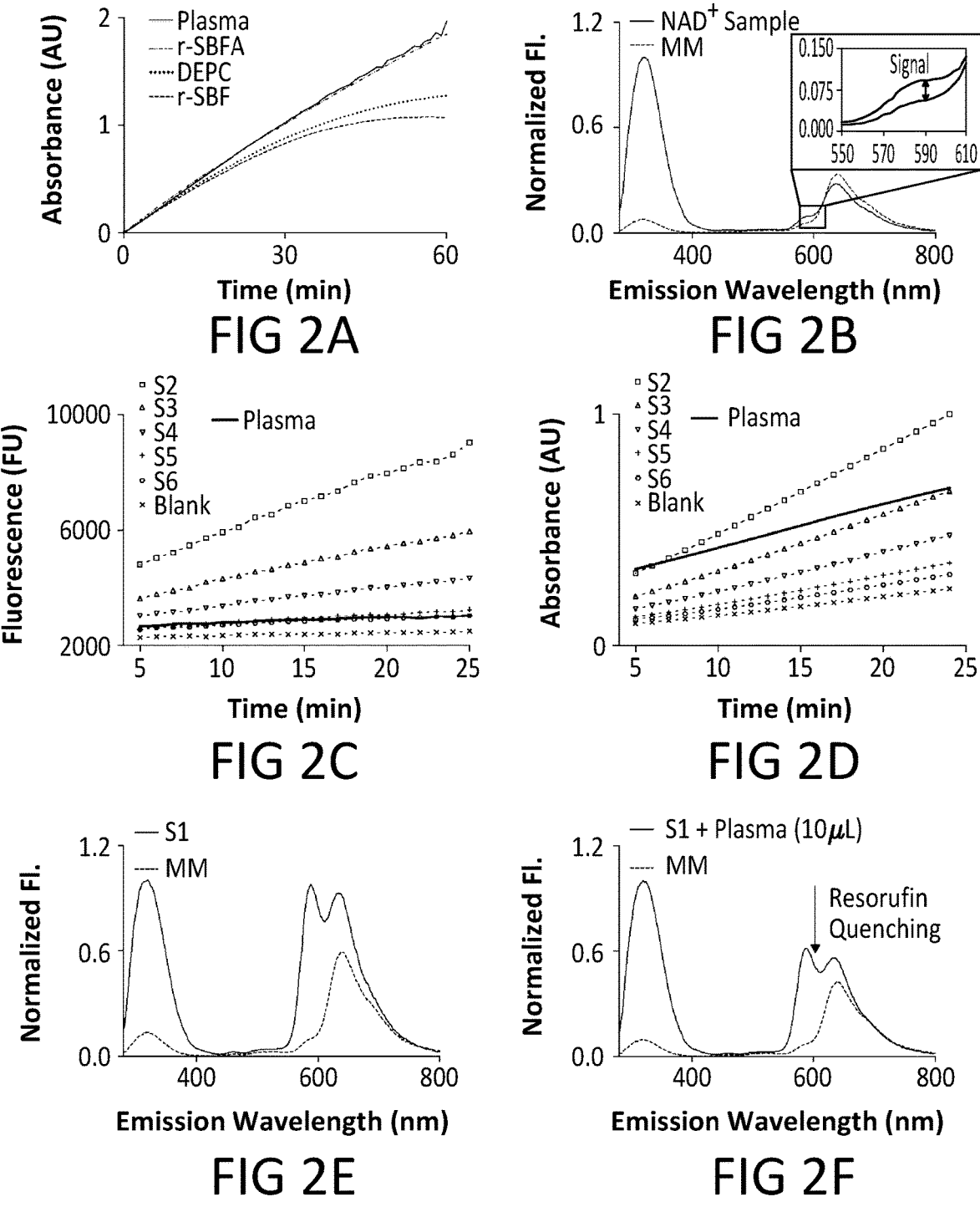
FIGS. 2A-2F: Overview of the spectroscopic techniques.

The advantages of fluorimetric over colorimetric detection techniques are well known and include a higher sensitivity and specificity as well as a lower limit of detection. Therefore, it was evaluated whether a fluorimetric method was superior to the colorimetric method. For this purpose, MTT was used for absorbance and resazurin for fluorescence, both representing the signal generating molecules. Since the signal of interest arises from the fluorophore ejection from resorufin at a wavelength of 590 nm, an autofluorescence scan of both, a respective "master mix" (MM) and a human heparinised plasma sample was performed and the results are shown in FIG. 2B. Indeed, the relative autofluorescence spectra of the MM and plasma sample were found to differ only marginally from approximately 0.093 for the eNAD$^+$ plasma sample and 0.057 for the MM, yielding a signal to noise ratio (SNR) of 163%. The measured fluorescence unit (FU) and absorbance unit (AU) readings for β-NAD standards and human plasma are depicted in FIGS. 2C and 2D. Despite the apparent parallels of the colorimetric and fluorimetric standard traces of β-NAD at different concentrations, it was noted that the fluorescence plasma signal is apparently nullified. In contrast, the colorimetric detection method exhibited a strong signal for human plasma. In order to clarify this surprising finding, that is, the apparent resorufin signal quenching in plasma, several autofluorescence scans of the β-NAD standards, plasma samples and master mix (please see section Methods) were conducted and are provided in FIGS. 2E and 2F. The fact that a signal was obtainable from the β-NAD standards, yet was virtually absent from all plasma samples was further explored by comparing the autofluorescence spectra of the first β-NAD standard S1 (753.6 nM) to S1 spiked with a small (10 μL) quantity of plasma. Strikingly, the relative fluorescence signal at 590 nm was found to be 0.964 for S1 and 0.102 for the MM (945% SNR), which dropped sharply upon the addition of human plasma to 0.614, giving a 602% SNR (the first emission spike around 320 nm from formulations containing either albumin or plasma is in fact due to the autofluorescence of albumin itself, since its tyrosine side chains fluoresces at this specific wavelength). Moreover, human blood plasma is known to exhibit substantial autofluorescence around 500-600 nm due to physiologically occurring porphyrins.

In conclusion, it was found that the colorimetric method, displayed in FIG. 3, was superior to the fluorimetric alternative for the measurement of eNAD$^+$ in human heparinised plasma.

Reaction Time Scale and eNAD$^+$ Storage Stability

Reaction Velocity

To determine the time frame of the assay's linear operation, the absorbance readings for 8-NAD standards S1 (753.6 nM) to S6 (23.5 nM) are depicted in FIG. 4A. Clearly, the relative reaction velocity, $v_R$, of S1 decreased, adopting a fluctuating and turbulent behaviour after about min 30, as seen in FIGS. 4b and 4c, with the latter displaying the derivative of $V_R$, $a_R$. From this, a time frame of linear operation between min 5-25 of reaction time was determined.

Storage Stability

The stability of eNAD$^+$ in human plasma remains an elusive and vague topic of investigation, suffering from a substantial lack of literature. However, eNAD$^+$ can be hydrolysed or degraded by multiple enzymes in plasma, such as ADPribosyltransferases (ARTs), as well as NAD$^+$-dependent glycohydrolases (NADases). Also, analyte storage stability is important for investigational studies. Therefore, eNAD$^+$ storage stability in human heparinised plasma samples at −80° C. over the course of three months was tested, which is displayed in FIG. 4D. Indeed, no statistically significant difference was found between any of the measured timepoints, at a significance level of p<0.01, with the measured eNAD$^+$ concentration being (225.9±16.7) nM. Hence, eNAD$^+$ can be considered stable in frozen human heparinised plasma for at least three months at −80° C. These results were found to be in accordance with a murine study that demonstrated stability of eNAD$^+$ in frozen murine plasma for at least one week and the commercially available β-NAD, which was described to be stable for at least six months in aqueous solution.

Recapitulating, linear enzymatic behaviour was confirmed for min 5-25 of the assay reaction time and eNAD$^+$ was found to remain stable in frozen human heparinised plasma for at least three months.

Standard Linearity and Enzyme Kinetics

In order to accurately measure eNAD$^+$, the $v_R$ ratio of any two standards should behave identical to the ratio of their β-NAD concentrations. To examine this, the $v_R$ ratio of standard, n, and neighbour n+1, was defined to be:

$$\gamma n = v_{Rn+1}/v_{Rn}$$

Figure 5A:
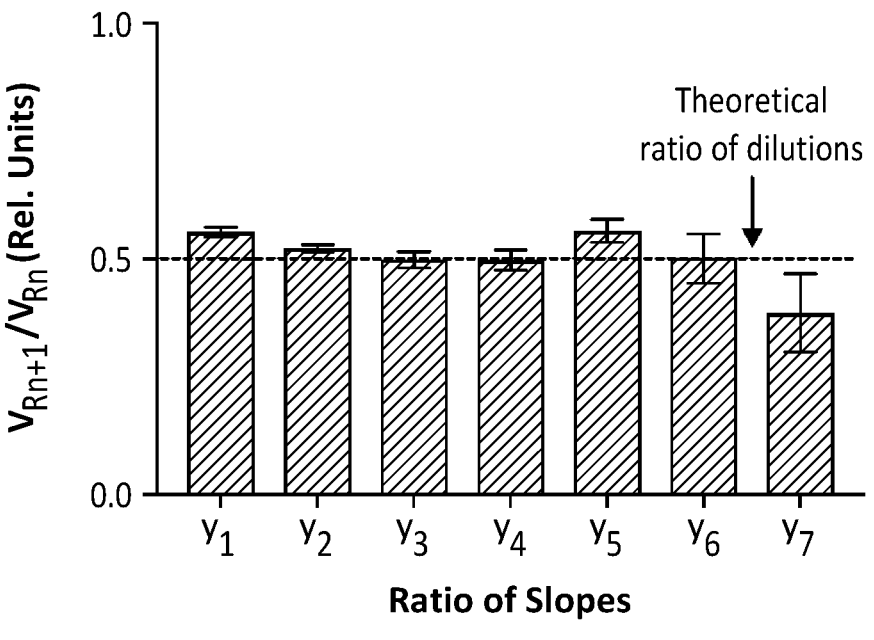
FIGS. 5A and B. NAD$^+$ assay linearity and enzyme kinetics.

The calculated results are presented in FIG. 5A. One can observe that γ remained relatively constant and closely resembled the 50% β-NAD standard dilutions for S1 (753.6 nM) to S7 (11.8 nM), with $\gamma_1$=0.556±0.011 to $\gamma_6$=0.501±0.052 and corresponding relative errors of $\delta_{\gamma1}$=1.96% and $\delta_{\gamma6}$=10.3%. However, there was an evident drop in the ratio when considering the change from S7 to S8 (5.9 nM), to $\gamma_7$=0.385±0.083, where the relative error increased to $\delta_{\gamma7}$=21.6%

Figure 5B:
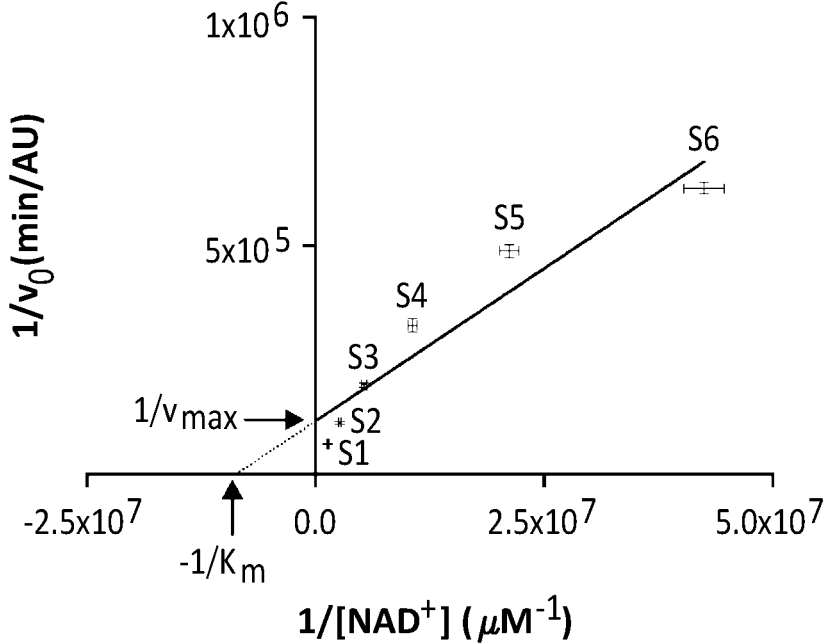
FIG. 5B The Lineweaver-Burk Plot constructed for averaged, blank corrected, v$_R$ data from eight Runs including S1-S6. n=8. Statistics: All error bars are given in terms of ±SD.

Moreover, $NAD^+$ was employed as the new substrate in the double reciprocal Lineweaver-Burke plot. The data displayed in FIG. 5B was constructed from eight independent assay reactions, where the Michaelis-Menten constant was found to be $K_m$=(115±45.6) nM in addition to the maximum reaction velocity being $v_{max}$=(8.58±3.13)μmol $min^{-1}$. In sum, the linear relationship between the standard slopes (γ) was confirmed for S1 (753.6 nM) down to S7 (11.8 nM), covering sufficiently the range of anticipated physiological concentrations of $PN^{ox}$.

Reliability of $PN^{ox}$ Detection in Relation to Albumin

Physiologically, serum albumin is the most abundant protein of human plasma. Patients with liver diseases can suffer from hypoalbuminaemia, presenting with levels below 35 g/L and drastic inter- as well as intrapatient variability, while healthy subjects typically feature levels in the range of 35-50 g/L. Hence, the effect of varying albumin concentrations on the assay's predictive capability was studied: An ordinary regression line that runs not through the origin (nTTO, $v'_R$=mx+$v_b$), as opposed to a regression line through the origin (TTO, $v_R$=mx+0), is subject to an inversely proportional relationship between the albumin concentration of the matrix and the calculated $eNAD^+$ value, rendering it unworkable for analysis.

In order to demonstrate this, we evaluated various r-SBFA matrices featuring 0 g/L (r-SBF), 10 g/L, 20 g/L, 30 g/L and 40 g/L of albumin. In fact, one can observe from FIG. 6A, where nTTO and TTO calibration curves are contrasted, that their slopes remained relatively constant with varying concentrations of albumin for m=(1.50±0.10) ngAUmL$^{-1}$min$^{-1}$ and m'=(1.51±0.12) ngAUmL$^{-1}$min$^{-1}$, respectively. The individual values for the slopes of the nTTO and TTO approach are displayed more precisely in FIG. 6B. Here, no statistically significant differences between the neighboring slopes of the physiological range of albumin concentrations (10 g/L-40 g/L) was found. However, FIG. 6A clearly demonstrates that an increase in the albumin concentration in the standard matrix caused an upward shift of the y-axis intercept, $v_b$, for lines constructed with a nTTO approach and is numerically presented in FIG. 6C, where the baseline can be seen to vary from $v_{b0}$=(−9.40±3.81)pgAUmL$^{-1}$min$^{-1}$ for no albumin (0 g/L) up to $v_{b40}$=(4.31±12.6)ngAUmL$^{-1}$ min$^{-1}$ for 40 g/L of albumin, with an average value of $v_b$=(4.31±12.6)ngAUmL$^{-1}$min$^{-1}$, indicating a relative error of $\delta_{vb}$=293%. No significant difference was found between $v_{b40}$ and $v_{b30}$ (p=0.0193) as well as $v_{b30}$ and $v_{b20}$ (p=0.0289), while $v_{b20}$ and $v_{b10}$ were, in fact, significantly different (p=0.0016). FIG. 6D reveals that the TTO method resulted in an average sample $NAD^+$ concentration of x'=193±17.0 nM, indicating a relative error of $\delta_x$=8.8% in contrast to x=183±47.4 nM for the nTTO approach, presenting with an escalated relative error of $\delta_x$=25.9%. Moreover, the TTO approach was fitted with an ordinary least squares regression, with CL=99%, to produce y'=−x0.34 nML/g+194 nM (R$^2$=0.7706), whilst the nTTO method featured y=−x2.84 nML/g+237 nM (R$^2$=0.9785), representing an approximately 8 times higher dependence of estimated $eNAD^+$ on albumin. When measuring the estimated $eNAD^+$ amounts, the TTO method far outperformed the nTTO method. Merely a concentration of 30 g/L of albumin let to an insignificant increase of the estimated $eNAD^+$ (p=0.0361), whilst 20 g/L (p=0.0049) and 10 g/L (p=0.0007) of albumin caused significantly different predicted $eNAD^+$ results. On the other hand, this effect was dampened when the TTO method was used as no significantly different estimated $eNAD^+$ concentrations were quantified at any of the given albumin concentrations, since p<0.01.

Taken together, differing serum albumin levels cause inaccurate estimations of sample $eNAD^+$ concentrations when the nTTO method is used. Strikingly, this effect was virtually eliminated, when calibration was constructed TTO, which lead to a substantially lower relative error as well as albumin related estimation bias.

Reproducibility, Sensitivity and Calibration

Figure 7A:
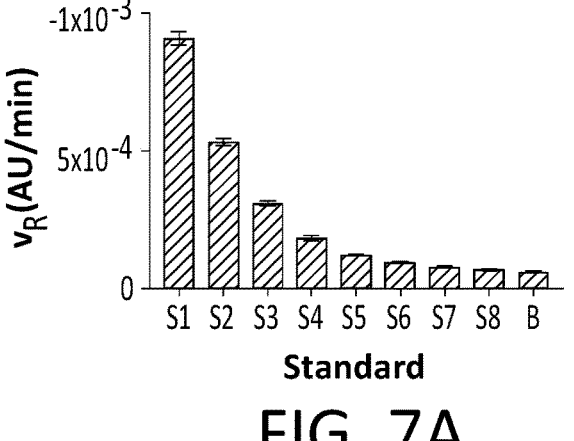
FIGS. 7A-7D. NAD$^+$ assay reproducibility.

For the sake of evaluating the repeatability and robustness of the assay, the complete method was independently carried out eight times, with the respective slopes of the standard curves calculated within the interval of min 5-25 of the reaction time. The corresponding results are given in terms of the relative reaction velocity for each β-NAD standard n, $v_{Rn}$, and are displayed in FIG. 7A. In descending order the relative reaction velocities of standards S1 (753.6 nM) to S8 (5.9 nM) as well as the blanks were determined to be $v_{R1}$=(9.10±0.28)×10$^{-4}$ AU/min for S1 down to $v_{RS8}$=(6.84±0.42)×10$^{-5}$ AU/min for S8 and $v_{RB}$=(6.18±0.33)× 10$^{-5}$ AU for the blank. The use of a two-way ANOVA (without repeated measures), adjusted with Tukey's multiple comparisons test, revealed that there was no significant difference observable between S6 (23.5 nM) and S7 (11.8 nM, p=0.012), S7 and S8 (5.9 nM, p=0.373), S7 and the blank (p=0.013), or S8 and the blank (p=0.876). In order to examine the potential implications for the precision of the assay when an additional β-NAD standard, n−1, was used for calibration, the ratio of the standard deviation, σ, to the difference in $v_R$, defines the introduced resolution error, ε:

$$\varepsilon_n = \frac{\sigma_n + \sigma_{n+1}}{v_{Rn} - v_{Rn-1}}$$

Figure 7B:
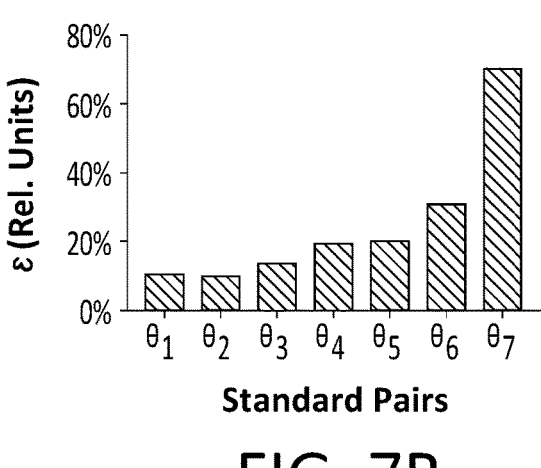

The respective values for c are depicted in FIG. 7B, where the resolution error introduced by the consideration of S1 through S6 was found to be below $\varepsilon_{1-5}$<20%, whereas the inclusion of S7 (11.8 nM) and S8 (5.9 nM) lead to an escalated resolution error of $\varepsilon_6$=30% and $\varepsilon_7$=70%, respectively. Having defined a threshold value of ε=20%, S7 and S8 were discarded from the assay for their lack of a statistically relevant $v_R$ and inflation of ε.

Figure 7C:
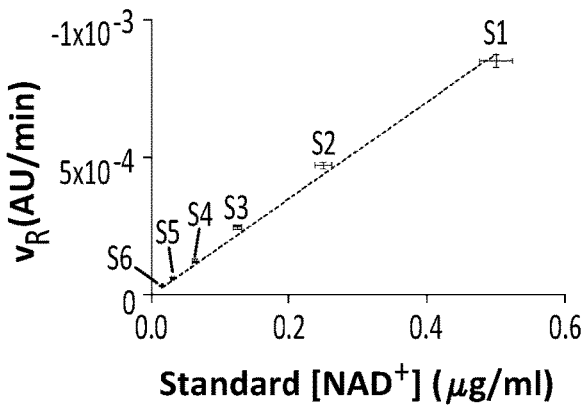

Following this discovery, an ordinary least squares linear regression fit of the blank adjusted standard calibration curve was constructed from S1-S6 to run through the origin (TTO), shown in FIG. 7c, where ρ=0.9984 and R$^2$=0.9969, with the corresponding slope m=(1.75±0.04) ngAUmL$^{-1}$ min$^{-1}$.

In order to present clinical findings of $eNAD^+$ concentrations in blood plasma, heparinised blood samples from 10 fasting patients were obtained, who were scheduled to receive hernioplasty. Subsequent to obtaining the plasma samples, we determined the $eNAD^+$ value to have a mean concentration of (305.2±32.2) nM (range: 240.9-342.7 nM).

20

Figure 7D:
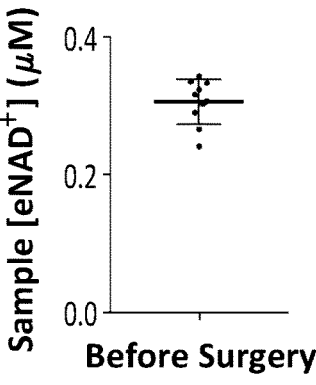

The graphical representation of this data is given in FIG. 7D. What is more, the analysis of one sample that was carried along all of the eight runs, resulted in a relative error of $\delta=8\%$ in the measured $eNAD^+$ concentration.

When combining these results, the method was able to sense $eNAD^+$ in human heparinised plasma and in standards featuring concentrations of 753.6 nM (S1) down to 23.5 nM (S6) maintaining a striking calibration precision yet exhibiting a minor relative error.

The presented method was exhaustively tested in human heparinised plasma and the analysis as well as the experimental protocol, SAMPLE $NP^{ox}$ ASSAY PROTOCOL (see also FIG. 1), below account for immense variations in the standard and sample matrices, due to albumin fluctuations.

In respect of the findings displayed in FIGS. 6A-D, it was evident that a regression line TTO would be used for all measurements, as it first and foremost increased the robustness of the method and secondly it was simply not feasible to produce a tailored albumin blank for every human heparinised plasma sample due to practical reasons. Moreover, albumin concentrations are rarely known, as they are not covered by standard blood chemistry tests. This, is as the evidence gathered and presented in FIGS. 6A and 6C, illustrates the high dependency of the y-axis intercept, $v_b$, of the assay's nTTO calibration curve on, in the context of this example, the albumin concentration of the standard matrix. Hence, when utilising those calibration curves to estimate the $eNAD^+$ of an actual plasma sample, one will obtain very uncertain and unreliable results, as $v_b$ in the equation of the regression line, when extrapolating for an unknown amount, x, takes the role as a subtractor of $v_R$, and, given that we are dealing with relatively small values of m in the denominator, causes escalated fluctuations of the resulting value. On a critical note, an estimation of the random error that arise when preparing the standards and the total random error, including the final addition of the MM to the standard, are given below. For this purpose, the common propagation of uncertainty analysis was conducted, where pipetting as well as applicable preparation errors, such as weighing scale or glassware uncertainties, were considered. For any given measurement of the experimental factors a, b and c resulting variable, Q, that is the combination of sums and differences, a+b, Q=a+b−c, the uncertainties, $\Delta$, add in quadrature, that is;

$$\Delta Q = \sqrt{(\Delta a)^2 + (\Delta b)^2 + (\Delta c)^2}$$

On the other hand, if R, is the resulting variable of a multiplication or division, R=(a+b)/c, then the fractional uncertainties add in quadrature;

$$\frac{\Delta Q}{Q} = \sqrt{\left(\frac{\Delta a}{a}\right)^2 + \left(\frac{\Delta b}{b}\right)^2 + \left(\frac{\Delta c}{c}\right)^2}$$

In fact, this resulted in the estimation of the random relative error in preparing S1 of $\delta_{S1}=4.84\%$, increasing to $\delta_{S6}=5.20\%$ for S6, while the total relative error after the addition of the MM for S1 was determined to be $\delta_{T1}=8.29\%$, increasing to $\delta_{T6}=8.50\%$ for S6. Obviously, this error can be minimised by preparing reagents in aliquots, where possible.

On a practical note, an experimenter is able to perform the whole method given in the SAMPLE $NP^{ox}$ ASSAY PROTOCOL, in approximately 90 min. When employing a commonly used 96 well plate this would imply a total experiment time of roughly 1 min per sample, representative of a substantial increase in time efficiency when compared to the commonly employed HPLC quantification methods, that usually require 10-60 min of reaction time per sample analysed. Also, as the person skilled in the art will readily recognize, automatization of the steps shown to be performed in an EPPENDORF tube, can further reduce the time to perform the assay.

At a molecular level, $PNs^{ox}$, in particular $eNAD^+$, has been identified to be involved in a substantial number of regulatory pathways as a coenzyme for ADPribosyltransferases (ARTs), $NAD^+$-dependent protein deacetylases of the Sir2 family (SIRTs) as well as $NAD^+$-dependent glycohydrolases (NADases), in addition to serving as a precursor of the calcium mobilising molecule cADPR (cyclic ADP-ribose). The highly modulating properties of $eNAD^+$ are highlighted by its substantial involvement in highly specific and selective ectoenzymes, namely NADases such as CD38, ADPribosyltransferases like ART2 or its key role in purinergic signalling through P2X7 or P2Y5. Leading on to the systemic involvement of $eNAD^+$ in immunological processes and its relevance to human physiology, the plasma membrane of eukaryotic cells was long believed to be impermeable to $NAD^+$. Yet, after some initial findings of passive pyridine nucleotide transmembrane-transport, Bruzzone et al., 2000 successfully identified this elusive $NAD^+$ transporter as the hexametric hemichannel Cx43 (Bruzzone et al., The FASEB J. 15, 10-12 (2000). Cx43 is a ubiquitous transmembrane protein, that, when juxtaposed on adjacent cells, forms local high density areas at the gap junctions between these cell.

Methods

Establishment of the Cycling Method

The protein alcohol dehydrogenase (ADH, EC1.1.1.1) from *Saccharomyces cerevisiae* was employed to measure the pyridine nucleotides $NAD^+$ and NADH, due to its specificity for $NAD^+$ as a coenzyme, which, given the cycling nature of the application promotes NADH to the status of being a coenzyme as well. Illustratively, a schematic of the principle behind this cycling assay is provided in FIG. 3, where the reader can follow the path of the electrons which are transferred during one cycle of the assay. Initially, the $NAD^+$ dependent dehydrogenase ADH catalyses the conversion of ethanol into acetaldehyde (ethanal) 20, reducing its coenzyme $NAD^+$ to NADH in the process. In turn, this reduced pyridine nucleotide donates an electron to the secondary redox indicator dye, 3-(4,5-dimethylthiazol-2-yl)-2,5-diphenyltetrazolium bromide (MTT), via a preceding coupled reaction with the primary indicator dye, phenazine methosulfate (PMS). The reduction of MTT, and subsequent formation of formazan, can then be assayed colorimetrically and linked to the concentration of $NAD^+$ (and NADH). In order to distinguish NAD+ from NADH, the impeccable works of Lowry et al., J. Biol. Chem. 236, 2756-2759 (1961) on 'The Stability of Pyridine Nucleotides', provided a method of extracting the respective nucleotides by means of heat-incubating them in different pH milieus. Thereby, $NAD^+$ could be extracted through the addition of a strong acid, destroying all NADH molecules (whereas NADH is extracted with a strong base, destroying all $NAD^+$ molecules). The extraction steps were chosen to feature pH 1.5 for the $NAD^+$ extraction. In order to enzymatically measure the respective pyridine nucleotides, the samples were neutralised at pH 7.4 in order to shift the pH into the physiological working range of ADH. The role of r-SBFA in this method was to emulate heparinised blood plasma as the standard matrix.

Preparation of Chemicals

The assay reaction was initialised, and thus the signal was induced through a Master Mix (MM), which, apart from $NAD^+$, contained all the molecules required for the cycling reaction which consisted of the following reagents: Alcohol Dehydrogenase from yeast in suspension, EC1.1.1.1 (ADH, SIGMA, USA, Catalogue No: 10127558001), thiazolyl blue tetrazolium bromide (MTT, Sigma, USA, Catalogue No: M2128), phenazine methosulfate (PMS, Sigma, USA, Catalogue No: P9625), ethanol (100%), Triethanolamine (TEA, Sigma, USA, Catalogue No: 90279), and diethyl dicarbonate (DEPC, Sigma, USA, Catalogue No: D5758) water. As employed in the MM, the TEA buffer, as well as the ADH solution were prepared in a ten-fold dilution with DEPC water, whilst PMS was prepared as a 10 mg/mL solution and MTT as a 1 mg/mL solution in DEPC water. In Table 2, a list of materials is given, featuring the molar make-up of the MM and the respective quantities of the molecules employed for a single well (150 µl of MM) and extended to an entire plate (extended to 105 wells, to facilitate the use of a pipetting basin). Upon the evaluation of a fluorimetric method, MTT was substituted with resazurin (SIGMA, USA, Catalogue No: R7017).

TABLE 2

List of materials used for the preparation of 150 µL master mix (MM) per well, scaled to fit a standard 96 well plate (where 105 wells are considered necessary for the use of a pipetting basin). Note that the reagents employed have been preciously diluted and weighed into DEPC water.

| Reagent | Q (µmol) | Well (µL) | Plate (µL) |
|---------|----------|-----------|------------|
| TEA | 25.72 | 33.6 | 3528 |
| EtOH | 129 | 7.5 | 788 |
| PMS | 0.4 | 12.3 | 1292 |
| MTT | 0.1 | 41.4 | 4347 |
| DEPC | — | 41.1 | 4316 |
| ADH | 125 U | 14.4 | 1512 |

N6522) as a reaction standard used for the construction of calibration curves. Firstly, a 1 mg/mL stock solution of β-NAD in DEPC water was prepared, followed by a thousand-fold dilution in DEPC water. Successively the first calibration standard (S1), was obtained to entail a concentration of 0.5 µg/mL (753.6 nM) by a further one to one dilution of 500 µL in 500 µL DEPC. Afterwards, 5 additional serial dilutions constituting 500 µL of previous Standard in 500 µL DEPC water were performed to obtain S2 (376.8 nM) through S6 (23.5 nM), respectively, forming a total of six calibration standards, which are summarised in Table 2. Initially, two further dilutions were prepared as S7 with a concentration of 11.8 nM and S8 with a concentration of 5.9 nM, however these were excluded from the assay upon evaluation of their suitability as calibration standards. Until use, prepared β-NAD aliquots were stored at −80° C.

Standard Matrix Preparation

When operating enzymatic assays, and subsequent sample concentration extrapolation using calibration curves, the standards (S1-S6) were carried in a matrix that adequately reflects and resembles the physiological properties of human blood plasma, the in vivo matrix of $eNAD^+$. Note that, deriving a plasma based standard matrix completely free of $NAD^+$ is generally not feasible because of the endogenous nature of this analyte. For this reason, several commonly used simulated body fluids (SBF) were theoretically compared to blood plasma based on their ionic composition and buffering capabilities, and are displayed in Table 3.

TABLE 3

Common simulated body fluids compared to human blood plasma: ionic concentrations are given in mM. See, Oyane et al. J. Biomed. Mater. Res. 64, 339-348 (2003).

| Formulation | $Na^+$ | $K^+$ | $Mg^{2+}$ | $Ca^+$ | $Cl^-$ | $HCO_3^-$ | $HPO_4^{2-}$ | $SO_4^{2-}$ | Buffer |
|-------------|--------|-------|-----------|--------|--------|-----------|--------------|-------------|--------|
| Blood Plasma | 142.0 | 5.0 | 1.5 | 2.5 | 103.0 | 27.0 | 1.0 | 0.5 | |
| Original SBF | 142.0 | 5.0 | 1.5 | 2.5 | 148.8 | 4.2 | 1.0 | 0.0 | Tris |
| Corrected (c-SBF) | 142.0 | 5.0 | 1.5 | 2.5 | 147.8 | 4.2 | 1.0 | 0.5 | Tris |
| Revised (r-SBF) | 142.0 | 5.0 | 1.5 | 2.5 | 103.0 | 27.0 | 1.0 | 0.5 | HEPES |
| Modified (m-SBF) | 142.0 | 5.0 | 1.5 | 2.5 | 103.0 | 10.0 | 1.0 | 0.5 | HEPES |

The $NAD^+$ and NADH extraction and neutralisation buffers were then prepared in DEPC water, where the $NAD^+$ extraction buffer consisted of a 0.3N HCl solution and the neutralisation buffer comprised equal parts of 0.36N TEA-HCl (ACROS, USA, Catalogue No: 170051000) and 0.6N KOH. Analogously, 0.3N KOH was used for the NADH extraction buffer, whilst the neutralisation buffer was composed of 23% 0.36N TEA-HCl, 23% 0.6N HCl and 54% DEPC water. PMS and MTT stock solutions were stored in aliquots at −20° C. until use. The MM was prepared freshly just prior to measurement to prevent auto-oxidation of PMS and MTT as well as a denaturation of ADH.

Preparation of Stock Solutions

The linearity, sensitivity, and specificity of the assay was determined with β-NAD (SIGMA, USA, Catalogue No:

Due to its remarkable ionic resemblance to blood plasma, we employed a revised simulated body fluid (r-SBF) to serve as the standard matrix. In addition to that, r-SBF contained HEPES buffer, which features an acid dissociation constant of $p_{ka}$=7.5, thus more closely resembling the buffering nature of plasma than the otherwise commonly used Tris buffer, exhibiting $pK_a$=8.07. Although the process for finding this standard matrix is presented and discussed in the following sections, it was found that the addition of albumin has proven crucial in emulating the assay's enzyme kinetics in human plasma. Finally, a list of materials used to prepare 1000 ml of a revised simulated body fluid adjusted with albumin (r-SBFA) in DEPC water is given in Table 4, below. In fact, the albumin concentrations of the r-SBFA were evaluated with respect to their impact upon the assay performance at 0 g/L (r-SBF), 10 g/L, 20 g/L, 30 g/L and 40 g/L. The prepared r-SBFA was stored in aliquots at –20° C., until use.

TABLE 4

List of materials used for the preparation of 1000 mL of a revised simulated body fluid adjusted with albumin (r-SBFA); the pH was adjusted to be 7.5, using approximately 0.8 mL 1.0N NaOH. The composition of the r-SBF without albumin was adopted from Oyane et al. J. Biomed. Mater. Res. 64, 339-348 (2003).

| Reagent | Supplier | Amount (g) |
|---|---|---|
| NaCl | SIGMA, USA, Catalog No: DE71376 | 5.403 |
| NaHCO₃ | SIGMA, USA, Catalog No: DES5761 | 0.740 |
| Na2CO₃ | SIGMA, USA, Catalog No: DES7795 | 2.046 |
| KCl | ROTH, GER, Catalog No: 6781.1 | 0.225 |
| KH₂PO₄ | ROTH, GER, Catalog No: 3904.1 | 0.138 |
| MgCl₂ · 6H₂0 | ROTH, GER, Catalog No: HN03.1 | 0.311 |
| HEPES | ROTH, GER, Catalog No: 9105.4 | 11.928 |
| CaCl₂ × H₂0 | ROTH, GER, Catalog No: HN04.1 | 0.388 |
| Na₂SO₄ | SIGMA, USA, Catalog No: S6547 | 0.072 |
| BSA | SERVA, GER, Catalog No: 47330.03 | 40 |

Blood Sample Collection

Human peripheral venous blood from surgical patients, approved by the Charité ethics committee (Charité-Universitätsmedizin Berlin, Germany, EA1/291/17 and EA1/018/17), was collected—after having obtained informed consent—into lithium heparin, complying with local regulatory guidelines and the Declaration of Helsinki. Samples were promptly centrifuged at 2500 g for 15 min at 4° C. in order to separate the plasma from all corpuscular parts of the blood, which was successively collected and snap frozen in liquid nitrogen. The resulting plasma aliquots were then transferred to a –80° C. freezer, where they were stored until being assayed for eNAD⁺ concentrations. In addition to the storage time evaluated, literature provided sufficient evidence that eNAD⁺ in frozen plasma, as well as the commercially available β-NAD, used in this method, were stable under these conditions.

Extraction

As previously described, the extraction procedure of NAD⁺ was based on the findings of Lowry, J. Biol. Chem. 236, 2746-2755 (1961) and Lilius et al. Anal. Biochem. 99, 22-27 (1979) and O'Reilly & Niven, Can. J. Vet. Res. 67, 229-231 (2003). Heparin plasma samples were treated with 0.3N HCl to extract NAD⁺ and 0.3N KOH to extract NADH, following their collection from the –80° C. freezer and after subsequent thawing at room temperature. This is since NAD⁺ is known to be stable for at least half an hour at room temperature (Liang, X. et al., Bioanal. 6, 1445-1457 (2014). Initially, 300 μL of sample were transferred into a new tube for NAD⁺ extraction. Upon addition of the acid solutions for pyridine nucleotide extraction, the samples were vortexed and then incubated at 60° C. for 10 min. Following this, the samples were promptly equilibrated on ice for 10 min. Subsequently, the samples were neutralised so as they would exhibit ADH's optimum working pH of 7.4 through the addition of 300 μL of the respective neutralisation buffers. The resulting pH values after extraction were confirmed with a standard glass pH probe and the data is presented in Table 5. See also FIG. 1.

TABLE 5 pH extraction procedure to extract purified versions of the pyridine nucleotides, that is, NAD⁺ in consideration of Lowry, J. Biol. Chem. 236, 2746-2755 (1961) and Lilius et al. Anal. Biochem. 99, 22-27 (1979) in three-fold repetition

| Extraction Buffer added (mL) | NAD+ extraction (pH) |
|---|---|
| 0 mL (plasma pH) | $7.84 \pm 0.05$ |
| 1 mL | $4.96 \pm 0.06$ |
| 2 mL | $3.87 \pm 0.05$ |
| 3 mL | $2.10 \pm 0.03$ |
| 4 mL | $1.47 \pm 0.02$ |
| 5 mL | $1.24 \pm 0.01$ |
| 6 mL | $1.11 \pm 0.01$ |

Sample $PN^{ox}$-Extraction Protocol
1) Prepare Buffers in DEPC Water:
(a) Acid Preparation
   0.3N HCl
   0.6N HCl
(a) Base Preparation
   0.3N KOH
   0.6N KOH
(b) $ePN^{red}$ Removal Buffer
   0.3N HCl
(d) Neutralization Reagents
   TEA-HCl: 0.36N TEA-HCL, adjust pH to 7.4
   Buffer 0.36N TEA-HCl: 0.6N KOH (ratio 1:1)
(e) Mastermix (MM) Solutions
   TEA-Buffer: 1:10 dilution of TEA, adjust pH to 7.4
   ADH: 1:10 dilution of ADH suspension
   PMS: 10 mg mL solution
   MTT: 1 mg mL solution
   EtOH: use 100% solution no DEPC
2) Prepare $PN^{ox}$ Standard Matrix
   Prepare r-SBFA in 1000 ml DEPC, as listed below, add HEPES first, then proceed in order, adjust pH to 7.4.
   (a) NaCl: 5.403 g, NaHCO₃: 0.740 g, Na₂HCO₃: 2.046 g
   (b) KCl: 0.225 g, KH₂PO4: 0.138 g
   (c) MgCl₂·6H₂O: 0.311 g
   (d) HEPES: 11.928 g
   (e) CaCl₂·2H₂O: 0.388 g
   (f) Na₂SO₄: 0.072 g
   (g) BSA: 40 g
3) Standard Matrix Preparation
   Prepare a β-NAD standard dilution series in the following manner.
   (a) Prepare a 1 mg μmL solution of β-NAD in DEPC
   (b) Dilute β-NAD solution 1000 fold (10 μL solution in 9990 μL DEPC)
   (c) Dilute 500 μL in 500 μL DEPC to make standard 1 (S1) to standard 6 (S2):
   S1 Standard: 753.6 β-NAD (nM), 50.00 β-NAD (ng/mL)
   S2 Standard: 376.8 β-NAD (nM), 25.00 β-NAD (ng/mL)
   S3 Standard: 188.4 β-NAD (nM), 12.50 β-NAD (ng/mL)
   S4 Standard: 94.2 β-NAD (nM), 6.25 β-NAD (ng/mL)
   S5 Standard: 47.1 β-NAD (nM), 3.13 β-NAD (ng/mL)
   S6 Standard: 23.5 β-NAD (nM), 1.56 β-NAD (ng/mL)
4) NAD Assay Procedure
   (a) Get Heparin Plasma (sample) from –80° C., thaw at room temperature
   (b) Separate plasma sample for $ePN^{red}$ Removal
   Pipette 300 μL sample in the EPPENDORF tube for $ePN^{red}$ Removal
   (c) Prepare standard matrix for $ePN^{red}$ Removal (Blank)

Pipette 300 µL r-SBFA into an eppi (d) ePN$^{red}$ Removal

NAD: add 300 µL 0.3N HCl

NADH: add 300 µL 0.3N KOH r-SBFA: add 300 µL 0.3N HCl (e) Incubation

Incubate EPPENDORF tubes at 60° C. for 10 min in an EPPENDORF tube heater (f) Equilibration EPPENDORF tubes on ice for 10 min, (g) Neutralization NAD: add 300 µL NAD Neutralization Buffer r-SBFA: add 300 µL NAD Neutralization Buffer (h) Deproteinization Centrifuge EPPENDORF tubes at 16.000 g for 10 min at 4° C.

Transfer supernatant into new EPPENDORF tubes (i) Get a transparent multiwell plate and prepare wells in duplicates NAD: 50 µL of Sample and 45 µL of Blank (1:10 Dilution)

(j) Stop the time, add 150 µL MM to wells, resuspend twice!

(k) After 5 min, measure at 565 nm in a microplate reader such as a TECAN Microplate reader for 30 min, analyze results from 5-25 min (linear range)

Pipetting and Plate Reader Settings

Before beginning the assaying phase of the method, the MM was prepared on ice without MTT, PMS or ADH, in order to prevent auto-oxidation of PMS or MTT and denaturation of ADH. Prior to pipetting the samples into the plate, the neutralised samples were centrifuged at 16.000 g for 10 min at 4° C. and the supernatant was successively pipetted into the wells. Standard dilutions (S1 to S6) were supplemented with 50 µL of r-SBFA that had been extracted and neutralised in the same manner as the samples, to provide the standard matrix similar to human plasma. Analogously, 50 µL of DEPC water was added to the samples to be measured in order to simulate the DEPC used in the β-NAD standard dilutions. Subsequently, ADH, MTT and PMS were added to the MM, 150 µL of which was pipetted into every well, resuspending twice. Afterwards the plate was stored at room temperature in the dark for 5 min prior to assaying. The absorbance of the samples was then measured at 565 nm in the microplate reader Infinite® 200 PRO (TECAN, Switzerland) at a temperature of 25° C. to prevent significant build-up of bubbles, which occurred at 37° C. Moreover, the Infinite® 200 PRO further served to assess fluorescence at 590 nm and perform autofluorescence scans. All measurements were conducted in duplicates and averaged.

Enzyme Kinetics

Since NAD$^+$ is the coenzyme in the specific reaction between ADH and ethanol, one can consider the concentration of NAD$^+$ to be rate limiting as the ethanol concentration was chosen well beyond the point of saturation in the MM. NAD$^+$ can therefore be regarded as the new substrate and, consequentially, be used in a graphical method to obtain the Michaelis Menten constant, $K_m$, and the maximum reaction velocity, $v_{max}$, from the double reciprocal Lineweaver-Burke plot described in Lineweaver et al., 1934 (Lineweaver & Burk., J. Am. Chem. Soc. 56, 658-666 (1934)). Here, the y-axis is given by $v_{-1}$, and $v_0$ represents the initial reaction velocity and the x-axis is represented by $[NAD^+]^{-1}$, the reciprocal of the analyte concentration. The double reciprocal Lineweaver-Burk plot facilitated the graphical evaluation of the Michaelis Menten constant, $K_m$, given by the negative reciprocal of the x-axis intercept, in addition to the maximum reaction velocity, $v_{max}$, given by the reciprocal of the y-axis intercept.

Regression Analysis

As illustrated shortly, the use of an ordinary regression line not through the origin (nTTO, $v_R=mx+v_b$), as opposed to a regression line through the origin (TTO, $v_R=mx+0$), was subject to an increased baseline noise and higher eNAD$^+$ estimation bias, introduced by the varying albumin concentrations in the standard matrix. Thus, the TTO method allowed for an albumin independent quantification of eNAD$^+$. The relative reaction velocity, $v_R$, is made up of the y-axis intersection, $v_b$, and the slope of the absorbance curve, m.

Reliability, Reproducibility and Linearity

For the sake of evaluating the repeatability and robustness of the assay, a quantification of eNAD$^+$ in healthy human heparinised plasma was conducted with eight independent measurements, featuring the thorough and individual conductance of the complete and previously described experimental protocol, including eight independent standard dilutions, as well as eight individually collected human heparinised plasma samples from a singular subject. Subsequently, these data were utilised to obtain the interval were the enzyme kinetics of the assay reaction occurred in a linear fashion, as well as to confirm the linear relationship between the standard β-NAD sequential dilutions and their respective relative reaction velocities.

NAD$^+$ Storage Stability

Being of considerable controversy, the stability of eNAD$^+$ in frozen plasma suffers from a definitive lack of data in the literature. However, upon the conductance of studies involving human samples, such knowledge is not only of paramount ethical importance but also crucial for the validity of designed experiments, in particular for the algorithm used to store such samples. Therefore, healthy human heparinised plasma samples were prepared and stored at −80° C. as described above, before being assayed for eNAD$^+$. The baseline measurement consisted of an immediate thawing and assaying of the first sample, whilst additional measurements were performed up to three months.

Evaluation of a Fluorimetric Alternative

In consideration of Rhodes et al., 1968, the ability of a fluorimetric method to sense eNAD$^+$ in human heparinised plasma was explored (Rhodes & Wooltorton, Phytochem. 7, 337-353 (1968)). For this purpose, we replaced MTT in the MM of the colorimetric method with resazurin, which, upon being reduced, forms the highly red fluorescing resorufin. Moreover, we paid close attention to conserve the number of moles of resazurin compared to MTT participating in the reaction as well as the volume of all suspensions that are part of the MM.

Statistics

Statistical analysis was conducted in Graphpad's Prism 7 (GraphPad Software, La Jolla, CA, USA). Concerning the evaluation of the eNAD$^+$ storage stability, the data were analysed using a two-tailed, paired t-test with confidence limits of CL=99%, as well as a two-way ANOVA (without repeated measures) adjusted with Tukey's multiple comparisons test featuring CL=99%. The statistical evaluation of the assay's dependence upon the albumin concentration of the standard matrix was conducted using a two-tailed, unpaired t-test with the confidence limits of CL=99%. With regards to the reproducibility of the aforementioned method, significance was assessed between two neighbouring standard signals using two different methods, namely a simple, two-tailed, unpaired t-test with the confidence limits of CL=99%, as well as using the more stringent conditions of a two-way ANOVA (without repeated measures) adjusted with Tukey's multiple comparisons test with CL=99%. Regression analysis of the calibration working curve was performed with the gold standard of an ordinary least squares fit, yielding a Pearson Correlation Coefficient, p, as well as a coefficient of determination, $R^2$, with CL=99%. Overall, an alpha value of p<0.01 was applied.

While the foregoing is directed to aspects of the present disclosure, other and further aspects of the disclosure can be devised without departing from the basic scope thereof, and the scope thereof is determined by the claims that follow.

What we claim is:

1. Method for determining a concentration of oxidized extracellular pyridine nucleotide ($ePN^{ox}$) in a body fluid of a subject, comprising:
   a) providing the body fluid comprising the $ePN^{ox}$ and reduced extracellular pyridine nucleotide ($ePN^{red}$) and subjecting the body fluid to an extraction, wherein the extraction removes the $ePN^{red}$ from the body fluid to result in an extracted body fluid comprising $ePN^{ox}$ and none or negligible amounts of $ePN^{red}$,
   b) providing more than one pyridine nucleotide standard (PN standard) comprising aliquots of a standard matrix of the body fluid mixed with a known concentration of a pyridine nucleotide which are each subjected or have been subjected to an extraction, wherein the extraction removes or removed the $ePN^{red}$ from the PN standard to result in an extracted PN standard comprising $ePN^{ox}$ and none or negligible amounts of $ePN^{red}$,
   c) providing an oxidoreductase, a substrate of the oxidoreductase and at least one primary and at least one secondary redox indicator dye to the extracted body fluid of a) and each of the extracted PN standards of b) and subjecting the extracted body fluid and the extracted PN standards, respectively of a) and b) to a cycling process, wherein the cycling process comprises one or more cycles of:
      the oxidoreductase reducing the $ePN^{ox}$ in the extracted body fluid of a) with a relative reaction velocity ($V_R$) and in each of the extracted PN standards of b) to produce $ePN^{red}$, wherein an electron is donated to the at least one primary redox indicator dye and subsequently to the at least one secondary redox indicator dye having an absorbance resulting in a change of the absorbance of the at least one secondary redox indicator dye,
   d) subsequently measuring the change in absorbance of the at least one secondary redox indicator dye in the extracted body fluid in which the $ePN^{ox}$ was reduced to determine the $V_R$ in the extracted body fluid and measuring the change in absorbance of the at least one secondary redox indicator dye in each of the extracted PN standards in which the $ePN^{ox}$ was reduced to determine the $V_R$ in each of the extracted PN standards and determining the concentration of the $ePN^{ox}$ in the body fluid of the subject provided in a) based on the $V_R$ measured in the extracted body fluid relative to the $V_R$ measured in each of the extracted PN standards.

2. The method of claim 1, wherein the extraction in a) comprises:
   removal of corpuscular parts including cells present in the body fluid via centrifugation at a centrifugal force of between 1500 g and 3500 g for 5-30 mins at below 25° C.

3. The method of claim 1 wherein
   the extractions in a) and b) comprises: providing (i) the body fluid or (ii) the body fluid after removal of corpuscular parts and subjecting (i) or (ii) and each of the PN standards (iii) to acidic conditions to reduce the pH of (i) or (ii) and (iii) to less than 5, 4, 3, 2 or 1.5, optionally followed by subjecting (i) or (ii) and (iii) to an elevated temperature and neutralizing (i) or (ii) to increase the pH to above 6, 7, 8 or 7.5.

4. The method of claim 3, wherein subjecting (i) or (ii) and (iii) to acidic conditions comprises adding an acid solution to (i) or (ii) and (iii).

5. The method of claim 4, wherein the acid solution is HCl.

6. The method of claim 3, wherein (i) or (ii) and (iii) are subjected to the elevated temperature and the elevated temperature is a temperature above 50 degrees Celsius and neutralizing (i) or (ii) and (iii) to increase the pH to above 6, 7, 8 or 7.5.

7. The method of claim 3, wherein the neutralizing comprises adding a neutralizing buffer.

8. The method of claim 1, wherein the subject has been subject to administration of PN (pyridine nucleotide) supplement for at least 1 week, 2 weeks, 3 weeks, 4 weeks, 2 months, or 3 months.

9. The method of claim 8, wherein the concentration of $ePN^{ox}$ is compared to a base value of $ePN^{ox}$ in the body fluid of the subject prior to administration of the PN supplement.

10. The method of claim 1, wherein the oxidoreductase is a reductase.

11. The method of claim 1, wherein the oxidoreductase is a dehydrogenase.

12. The method of claim 11, wherein the dehydrogenase is an alcohol dehydrogenase (ADH), optionally from *Saccharomyces cerevisiae*.

13. The method of claim 12, wherein the standard matrix of the body fluid for each of the more than one PN standard comprise, per 1000 ml, between 10 and 100 g of albumin which provides zinc to the ADH.

14. The method of claim 1, wherein the standard matrix comprises albumin.

15. The method of claim 14, wherein the body fluid is saliva, urine, lymph, serum or plasma.

16. The method of claim 1, wherein the standard matrix has:
   an optical density that is between 95% and 105% of the optical density of the body fluid;
   a $pK_a$ value that deviates from the $pK_a$ value of the body fluid by not more than 5, 4, 3, 2 or 1;
   an ionic composition that corresponds to that of the body fluid in at least two ions; and
   further comprises at least one donor of a trace element of an oxidoreductase.

17. The method of claim 16, wherein the ionic composition of the standard matrix corresponds to that of the body fluid in at least three ions.

18. The method of claim 1, wherein each of the more than one PN standards in b) comprises from 20 nM to 800 nM pyridine nucleotide.

19. The method of claim 18, wherein the pyridine nucleotide in the PN standards is β-NAD.

20. The method of claim 1, wherein the standard matrix has a $pK_a$ value which is maintained by HEPES (4-(2-hydroxyethyl)-1-piperazineethanesulfonic acid).

21. The method of claim 1, wherein the oxidized extracellular pyridine nucleotide is $eNAD^+$ (oxidized extracellular nicotinamide adenine dinucleotide) or eNADP$^+$ (oxidized extracellular nicotinamide adenine dinucleotide phosphate).

22. The method of claim 1, wherein the at least one primary redox indicator dye is phenazine methosulfate (PMS) and the at least one secondary redox indicator dye is 3-(4,5-dimethylthiazol-2-yl)-2,5-diphenyltetrazolium bromide (MTT) or a tetrazolium salt thereof.

23. The method of claim 1, wherein the extraction comprises:

providing (i) the body fluid or (ii) the body fluid after removal of corpuscular parts and subjecting (i) or (ii) to acidic conditions to reduce the pH of (i) or (ii) to less than 5 followed by subjecting (i) or (ii) to an elevated temperature and neutralizing (i) or (ii) to increase the pH to above 6.

24. The method of claim 1, wherein the body fluid has not been in contact with and is free of EDTA (ethylenediaminetetraacetic acid).

25. The method of claim 1, wherein the standard matrix of the body fluid for each of the more than one PN standard has a pH value of between 7 and 8 and, per 1000 ml, between 10 g and 100 g of a carrier of a trace element.

26. The method of claim 25, wherein a standard calibration curve is constructed from the $V_R$ for each of the extracted PN standards for quantifying the ePN$^{ox}$ in the body fluid in d), wherein the standard calibration curve is established using a master mix comprising the oxidoreductase, the substrate of the oxidoreductase, the at least one primary redox indicator dye and/or the at least one secondary redox indicator dye.

27. The method of claim 26, wherein the standard calibration curve is a regression line that runs through the origin (TTO).

28. The method of claim 26, wherein the standard calibration curve is a regression line that runs not through the origin (nTTO).

29. The method of claim 1, wherein the extraction each of the more than one PN standard in b) is subjected to corresponds to the extraction the body fluid in a) is subjected to.

30. The method of claim 1, wherein the body fluid subsequent to the extraction in a) comprises no intracellular pyridine nucleotides (iPNs) or substantially no iPNs.

31. The method of claim 1, wherein each of the more than one PN standard has a pH value of between 7.3 and 7.7.

* * * * *